United States Patent
Masuno et al.

(10) Patent No.: US 10,407,547 B2
(45) Date of Patent: Sep. 10, 2019

(54) METHODS OF PRODUCING COMPOUNDS FROM 5-(HALOMETHYL)FURFURAL

(71) Applicant: MICROMIDAS, INC., West Sacramento, CA (US)

(72) Inventors: Makoto Nathanael Masuno, Elk Grove, CA (US); Dimitri A. Hirsch-Weil, Sacramento, CA (US); Ryan L. Smith, Sacramento, CA (US); John Albert Bissell, II, Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 15/310,728

(22) PCT Filed: May 12, 2015

(86) PCT No.: PCT/US2015/030364
§ 371 (c)(1),
(2) Date: Nov. 11, 2016

(87) PCT Pub. No.: WO2015/175528
PCT Pub. Date: Nov. 19, 2015

(65) Prior Publication Data
US 2017/0081470 A1    Mar. 23, 2017

Related U.S. Application Data

(60) Provisional application No. 61/992,060, filed on May 12, 2014.

(51) Int. Cl.
| | | |
|---|---|---|
| *C07D 307/16* | (2006.01) | |
| *C08G 69/08* | (2006.01) | |
| *C07C 209/68* | (2006.01) | |
| *C08G 69/04* | (2006.01) | |
| *C08G 69/26* | (2006.01) | |
| *C08G 69/28* | (2006.01) | |
| *C07C 29/132* | (2006.01) | |
| *C07C 29/149* | (2006.01) | |
| *C07C 45/29* | (2006.01) | |
| *C07C 45/66* | (2006.01) | |
| *C07D 223/10* | (2006.01) | |
| *C07D 307/52* | (2006.01) | |

(52) U.S. Cl.
CPC .......... *C08G 69/08* (2013.01); *C07C 29/132* (2013.01); *C07C 29/149* (2013.01); *C07C 45/29* (2013.01); *C07C 45/66* (2013.01); *C07C 209/68* (2013.01); *C07D 223/10* (2013.01); *C07D 307/16* (2013.01); *C07D 307/52* (2013.01); *C08G 69/04* (2013.01); *C08G 69/26* (2013.01); *C08G 69/28* (2013.01); *C07C 2601/14* (2017.05)

(58) Field of Classification Search
CPC ................................................... C07D 307/16
See application file for complete search history.

(56) References Cited

U.S. PATENT DOCUMENTS

| | | |
|---|---|---|
| 2005/0032707 A1 | 2/2005 | Prasad et al. |
| 2006/0004088 A1 | 1/2006 | Kim et al. |
| 2007/0106024 A1 | 5/2007 | Tsou et al. |
| 2007/0112225 A1 | 5/2007 | Sirch et al. |
| 2008/0064902 A1 | 3/2008 | Leconte et al. |
| 2010/0062276 A1 | 3/2010 | Van Rhijn |
| 2010/0317069 A1 | 12/2010 | Burk et al. |
| 2012/0035399 A1 | 2/2012 | Abillard et al. |
| 2012/0070592 A1 | 3/2012 | Stall et al. |
| 2012/0142886 A1 | 6/2012 | Frost |
| 2013/0085255 A1 | 4/2013 | Coudray et al. |
| 2013/0184495 A1 | 7/2013 | Dias et al. |
| 2013/0245316 A1 | 9/2013 | Masuno et al. |
| 2013/0267719 A1 | 10/2013 | Mikochik et al. |
| 2013/0303723 A1 | 11/2013 | Burk et al. |
| 2014/0100378 A1 | 4/2014 | Masuno et al. |

FOREIGN PATENT DOCUMENTS

| | | |
|---|---|---|
| CN | 101137608 A | 3/2008 |
| CN | 100439304 C | 12/2008 |
| CN | 101878208 A | 11/2010 |
| DE | 1013425 | 8/1957 |
| JP | 11-180937 A | 7/1999 |
| WO | 2003/024955 A2 | 3/2003 |
| WO | 2007/147804 A1 | 12/2007 |
| WO | 2009/103560 A1 | 8/2009 |
| WO | 2011/096812 A1 | 8/2011 |
| WO | 2012/170520 A1 | 12/2012 |
| WO | 2014/043468 A1 | 3/2014 |
| WO | 2014/066746 A1 | 5/2014 |
| WO | 2015/060829 A1 | 4/2015 |

OTHER PUBLICATIONS

Morrison. Organic Chemistry, fourth edition, 1983, pp. 206-207 and 898-900.*
Buntara et al., "Caprolactam from Renewable Resources: Catalytic Conversion of 5-Hydroxymethylfurfural into Caprolactone" Angewandte Chemie International Ed., vol. 50, 2011, pp. 7083-7087.
Fenton et al., "LXXXV—Derivatives of Methylfurfural", Journal of the Chemical Society, Transactions, vol. 79, Jan. 1, 1901, pp. 807-816.
Fenton et al. "XLI.—Bromomethylfurfuraldehyde", Journal of the Chemical Society, Transactions, vol. 75, Jan. 1, 1899, pp. 423-433.
Hawker et al., "Synthesis and Evaluation of Novel Heteroaromatic Substrates of GABA Aminotransferase", Bioorganic and Medicinal Chemistry, vol. 20, No. 19, Oct. 1, 2012, pp. 5763-5773.

(Continued)

*Primary Examiner* — Noble E Jarrell
(74) *Attorney, Agent, or Firm* — Morrison & Foerster LLP

(57) ABSTRACT

Provided herein are methods of producing compounds, such as cyclohexanone, hexanediamine, hexanediol, hexamethylenediamine, caprolactam and nylon, from 5-(halomethyl) furfural.

9 Claims, 6 Drawing Sheets

(56) References Cited

OTHER PUBLICATIONS

Hibbert et al., "Studies on Cellulose Chemistry II. The Action of Dry Hydrogen Bromide on Carbohydrates and Polysaccharides1,2", Journal of the American Chemical Society, vol. 45, 1923, pp. 176-182.

International Preliminary Report on Patentability received for PCT Application No. PCT/US2015/030364, dated Nov. 24, 2016, 14 pages.

International Search Report and Written Opinion received for PCT Patent Application No. PCT/US2015/030364, dated Jul. 30, 2015, 17 pages.

Lapina et al., "Reactions of Alkyl (Halomethyl) Furancarboxylates with Hexamethylenetetramine", Russian Journal of General Chemistry, vol. 76, No. 8, 2006, pp. 1304-1309.

Liu et al., "Theoretical Studies on Thermochemistry for Conversion of 5-Chloromethylfurfural into Valuable Chemicals", The Journal of Physical Chemistry A, vol. 115, No. 46, Nov. 24, 2011, pp. 13628-13641.

Mascal et al., "Dramatic Advancements in the Saccharide to 5-(Chloromethyl)furfural Conversion Reaction", Chemsuschem, vol. 2, 2009, pp. 859-861.

Ogawa et al., "The Structure of an Antibiotic Kanamycin", Bulletin of the Agricultural Chemical Society of Japan, vol. 23, No. 4, 1959, pp. 289-310.

Shmagina et al., "Preparation of 5-Aminomethyl-2-Furancarboxylic Acid and its Butyl Ether", Body of the State Chemical Industry COM.ITE / Gagosplane USSR, No. 1, Mar. 28, 1965, pp. 44-46. (See Communication Under 37 CFR § 1.98(a) (3)).

Singh et al., "Preferential Polymerization of 5-(Aminomethyl)-2-Furancarboxylic Acid (Amfc) Into a Cyclic Tripeptide", Journal of Theoretical and Computational Chemistry vol. 03, 2004, pp. 555.

Szmant et al., "The Preparation of 5-Chloromethylfurfuraldehyde from High Fructose Corn Syrup and other Carbohydrates", Journal of Chemical Technology and Biotechnology, vol. 31, 1981, pp. 205-212.

Prasad et al., "Furanoid Sugar Amino Acids as Dipeptide Mimics in Design of Analogs of Vasoactive Intestinal Peptide Receptor Binding Inhibitor", Journal of Peptide Research, vol. 66, 2005, pp. 75-84.

Kiruthika et al., "CuI-Catalyzed Coupling of gem-Dibromovinylanilides and Sulfonamides: An Efficient Method for the Synthesis of 2-Amidoindoles and Indolo[1,2-a]quinazolines", Org. Lett., vol. 16, Dec. 30, 2013, pp. 484-487.

* cited by examiner

METHODS OF PRODUCING COMPOUNDS FROM 5-(HALOMETHYL)FURFURAL

CROSS-REFERENCE TO RELATED APPLICATIONS

This application is a U.S. National Phase patent application of PCT/US2015/030364, filed May 12, 2015, which claims priority to U.S. Provisional Patent Application No. 61/992,060, filed May 12, 2014, the disclosures of which are herein incorporated by reference in their entirety.

FIELD

The present disclosure relates generally to methods of producing one or more compounds from 5-(halomethyl)furfural, and more specifically to methods of producing cyclohexanone, hexanediamine, hexanediol, hexamethylenediamine, caprolactam and nylon from 5-(chloromethyl)furfural.

BACKGROUND 5-(Halomethyl)furfural may be obtained from renewable sources, such as biomass, and may be used to produce a variety of bio-based fuels, polymers, and other commodity and specialty chemicals. For example, 5-(halomethyl)furfural may be converted into 5-(ethoxymethyl)furfural or 5-methylfurfural, both of which may serve a precursor to produce biofuels. 5-(Halomethyl)furfural may also be converted to ethyl levulinate, which is a diesel oxygenate. 5-(Halomethyl)furfural may also be converted to levulinic acid, 5-(hydroxymethyl)furfural, and 2,5-furandicarboxylic acid which are known to be useful precursors to various chemicals. Thus, additional methods for expanding the platform of compounds that can be produced from 5-(halomethyl)furfural are needed.

BRIEF SUMMARY

Provided herein are methods of producing various compounds, including cyclohexanone, hexanediamine, hexanediol, hexamethylenediamine, caprolactam and nylon, from 5-(chloromethyl)furfural.

In one aspect, provided is a method of producing a compound of formula (D):

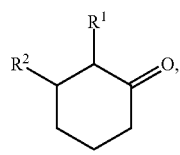

wherein $R^1$ and $R^2$ are each independently hydrogen or alkyl, by:
converting a compound of formula (A) to a compound of formula (B), wherein:
the compound of formula (A) is:

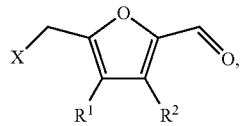

wherein:
$R^1$ and $R^2$ are as defined for formula (D) above, and
X is halo, and
the compound of formula (B) is:

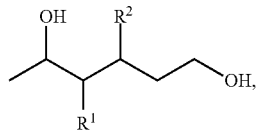

wherein $R^1$ and $R^2$ are as defined for formula (D) above;
oxidizing the compound of formula (B) to a compound of formula (C), wherein:
the compound of formula (C) is:

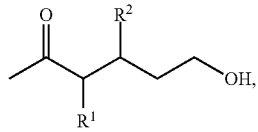

wherein $R^1$ and $R^2$ are as defined for formula (D) above; and
cyclizing the compound of formula (C) to produce the compound of formula (D).

In certain aspects, provided is a method of producing cyclohexanone, by:
converting 5-(halomethyl)furfural to hexane-1,5-diol;
oxidizing the hexane-1,5-diol to produce 6-hydroxyhexan-2-one; and
cyclizing the 6-hydroxyhexan-2-one to produce cyclohexanone.

In another aspect, provided is a method of producing a compound of formula (F):

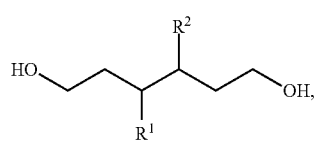

wherein $R^1$ and $R^2$ are each independently hydrogen or alkyl, by:
combining a compound of formula (A) with an alkanolate or acetate salt to produce a compound of formula (E), wherein:

the compound of formula (A) is:

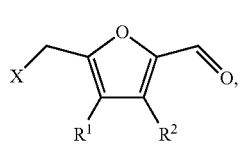

wherein:
R¹ and R² are as defined for formula (F) above, and
X is halo, and
the compound of formula (E) is:

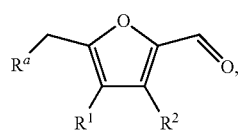

wherein:
R¹ and R² are as defined for formula (D) above, and
$R^a$ is O(alkyl) when an alkanolate salt is used, and $R^a$ is CO$_2$(alkyl) when an acetate salt is used; and
reducing the compound of formula (E) to produce the compound of formula (F).

In certain aspects, provided is a method of producing hexane-1,6-diol, by:
contacting 5-(halomethyl)furfural with an alkanolate or acetate salt to produce 5-(alkoxymethyl)furan-2-carbaldehyde; and
reducing the 5-(alkoxymethyl)furan-2-carbaldehyde to produce hexane-1,6-diol.

In yet another aspect, provided is a method of producing a compound of formula (I):

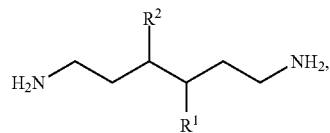

and/or a salt thereof, wherein R¹ and R² are each independently hydrogen or alkyl, by:
converting a compound of formula (A) to a compound of formula (H) and/or a salt thereof, wherein:
the compound of formula (A) is:

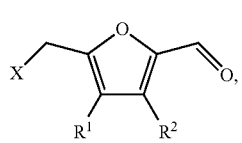

wherein:
R¹ and R² are as defined for formula (I) above, and
X is halo, and the compound of formula (H) is:

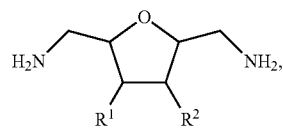

wherein R¹ and R² are as defined for formula (I) above; and
converting the compound of formula (H) and/or a salt thereof to the compound of formula (I) and/or a salt thereof.

In certain aspects, provided is a method of producing hexamethylenediamine, by:
converting 5-(halomethyl)furfural to (tetrahydrofuran-2,5-diyl)dimethanamine; and
converting the (tetrahydrofuran-2,5-diyl)dimethanamine to hexamethylenediamine.

In yet another aspect, provided is a method of producing a compound of formula (J):

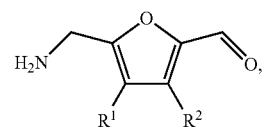

and/or a salt thereof, wherein R¹ and R² are each independently hydrogen or alkyl, by:
combining a compound of formula (A) with ammonia to form a reaction mixture, wherein:
the compound of formula (A) is:

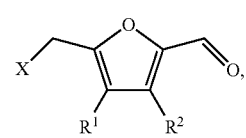

wherein:
R¹ and R² are as defined for formula (J) above, and
X is halo, and
producing the compound of formula (J) and/or a salt thereof from at least a portion of the reaction mixture.

In yet another aspect, provided is a method of producing a compound of formula (I):

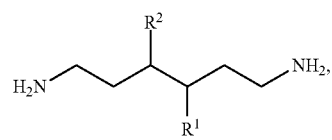

and/or a salt thereof, wherein R¹ and R² are each independently hydrogen or alkyl, by:
combining a compound of formula (A) with ammonia to produce a compound of formula (J) and/or a salt thereof, wherein:

the compound of formula (A) is:

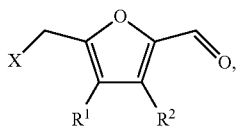
(A)

wherein:
$R^1$ and $R^2$ are as defined for formula (I) above, and
X is halo, and
the compound of formula (J) is:

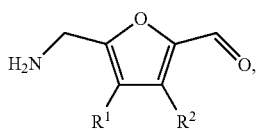
(J)

wherein $R^1$ and $R^2$ are as defined for formula (I) above;
reducing the compound of formula (J) and/or a salt thereof to produce a compound of formula (H) and/or a salt thereof, wherein:
the compound of formula (H) is:

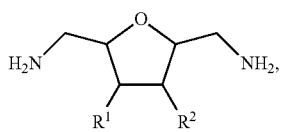
(H)

wherein $R^1$ and $R^2$ are as defined for formula (I) above; and
further reducing the compound of formula (H) and/or a salt thereof to produce the compound of formula (I) and/or a salt thereof.

In another aspect, provided is a method of producing a compound of formula (R):

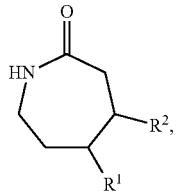
(R)

wherein $R^1$ and $R^2$ are each independently hydrogen or alkyl, by:
converting a compound of formula (A) to a compound of formula (P) and/or a salt thereof, wherein:

the compound of formula (A) is:

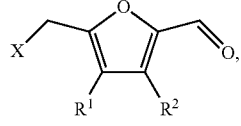
(A)

wherein:
$R^1$ and $R^2$ are as defined for formula (R) above, and
X is halo, and
the compound of formula (P) is:

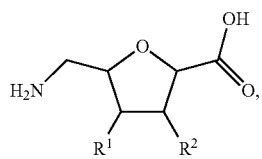
(P)

wherein $R^1$ and $R^2$ are as defined for formula (R) above; and
converting the compound of formula (P) and/or a salt thereof to the compound of formula (R).

In certain aspects, provided is a method for producing caprolactam, by:
converting 5-(halomethyl)furfural to 5-(aminomethyl)tetrahydrofuran-2-carboxylic acid; and
converting the 5-(aminomethyl)tetrahydrofuran-2-carboxylic acid to caprolactam.

In yet other aspects, provided is a method of producing a compound of formula (R):

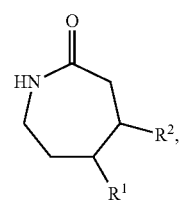
(R)

wherein $R^1$ and $R^2$ are each independently hydrogen or alkyl, by:
reducing a compound of formula (N-1) and/or a salt thereof to produce a compound of formula (P) and/or a salt thereof, wherein:
the compound of formula (N-1) is:

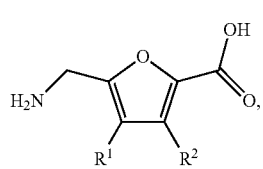
(N-1)

wherein $R^1$ and $R^2$ are as defined for formula (R) above, and the compound of formula (P) is:

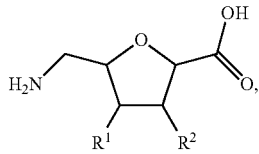

wherein $R^1$ and $R^2$ are as defined for formula (R) above; and converting the compound of formula (P) and/or salt thereof to the compound of formula (R).

In other aspects, provided is a method of producing a polymer of formula (V):

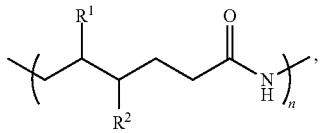

wherein:

$R^1$ and $R^2$ are each independently hydrogen or alkyl, and n is greater than 1, by:

polymerizing a compound of formula (N-1) and/or a salt thereof to produce a polymer of formula (T), wherein:

the compound of formula (N-1) is:

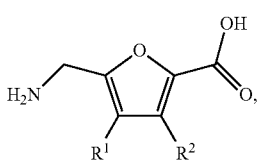

wherein $R^1$ and $R^2$ are as defined for formula (V) above, and the polymer of formula (T) is:

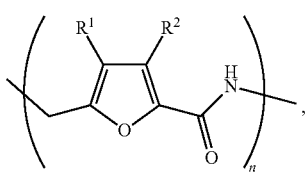

wherein $R^1$, $R^2$ and n are as defined for formula (V) above;

reducing the polymer of formula (T) to a polymer of formula (U), wherein:

the polymer of formula (U) is:

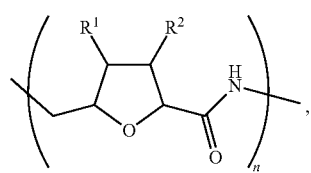

wherein $R^1$, $R^2$ and n are as defined for formula (V) above; and converting the polymer of formula (U) to the polymer of formula (V).

In yet other aspects, provided is a method of producing a polymer of formula (V):

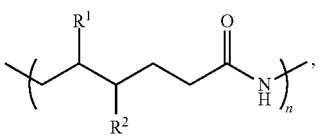

wherein:

$R^1$ and $R^2$ are each independently hydrogen or alkyl, and n is greater than 1, from a compound of formula (D), a compound of formula (F), a compound of formula (I), a compound of formula (R), or any combination thereof, produced according to any of the methods described herein.

In certain aspects, provided are also methods of producing nylon from the cyclohexanone, the hexane-1,6-diol, the hexamethylenediamine, the caprolactam, or any combination thereof, produced according to any of the methods described herein.

In some embodiments, provided is a method for producing nylon having the structure of formula (X):

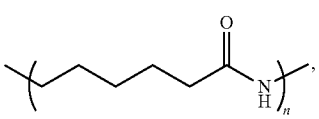

wherein n is an integer greater than 0;

by:

converting 5-(halomethyl)furfural to 5-(aminomethyl)furan-2-carboxylic acid; and polymerizing the 5-(aminomethyl)furan-2-carboxylic acid to form a polymer of formula (X1):

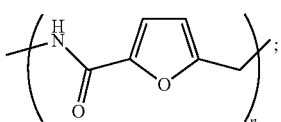

reducing the polymer of formula (X1) to form a polymer of formula (X2):

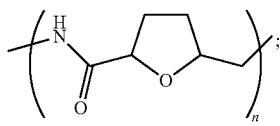

and converting the polymer of formula (X2) to the nylon of formula (X).

Provided herein are also the use of a compound of formula (D), a compound of formula (F), a compound of formula (I), a compound of formula (R), or any combination thereof, for the production of various polymers, including, for example, nylon.

In some aspects, provided herein are also compositions that include a compound of formula (D), a compound of formula (F), a compound of formula (I), a compound of formula (R), or any combination thereof, produced according to any of the methods described herein.

In certain aspects, provided herein are also compositions that include cyclohexanone, hexane-1,6-diol, hexamethylenediamine, caprolactam, or nylon produced according to any of the methods described herein.

DESCRIPTION OF THE FIGURES

The present application can be best understood by reference to the following description taken in conjunction with the accompanying figures, in which like parts may be referred to by like numerals.

DETAILED DESCRIPTION

Figure 1:
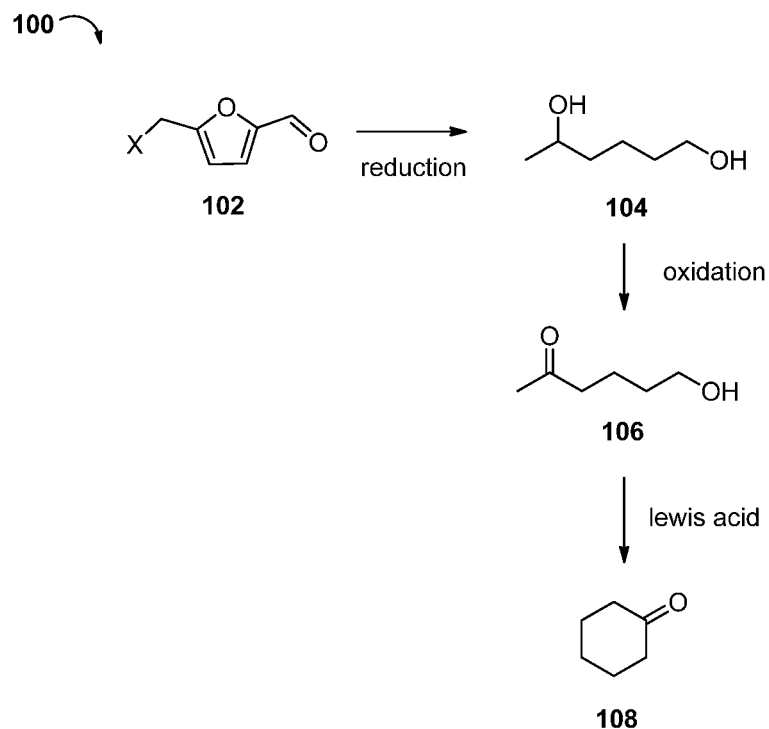
FIG. 1 depicts an exemplary scheme to produce cyclohexanone from 5-(halomethyl)furfural.

The following description sets forth exemplary methods, parameters and the like. It should be recognized, however, that such description is not intended as a limitation on the scope of the present disclosure but is instead provided as a description of exemplary embodiments.

Provided herein are methods of producing various compounds from 5-(halomethyl)furfural. Such compounds produced may include, for example, cyclohexanone, hexanediamine, hexanediol, hexamethylenediamine, caprolactam and nylon. Such compounds may be used as precursors to produce various products. For example, cyclohexanone, hexanediamine, hexanediol, hexamethylenediamine, and caprolactam may each serve as precursors for producing polymers, such as nylon.

The 5-(halomethyl)furfural used in the methods described herein may be provided by any commercially available sources or produced by any suitable methods known in the art. For example, 5-(halomethyl)furfural may be produced from sugars, cellulose or biomass. See e.g., WO 2012/170520; Mascal & Nikitin, *ChemSusChem* 2009, 2, 859; Szmant & Chundury, *J. Chem. Tech. Biotechnol.* 1981, 31, 205-212; Liu et al., *J. Phys. Chem. A*, 2011, 115, 13628-13641; Fenton and Gostling, *J. Chem. Soc., Trans.*, 1901, 79, 807-816; Fenton and Gostling, *J. Chem. Soc., Trans.*, 1899, 75, 423-433; and Hibbert and Hill, *J. Am. Chem. Soc.* 1922, 44, 176-182.

The methods to produce various compounds, including cyclohexanone, hexanediamine, hexanediol, hexamethylenediamine, caprolactam and nylon, from 5-(halomethyl)furfural are each described in further detail below.

Methods of Producing Compounds of Formula (D), Including, e.g., Cyclohexanone

In some aspects, provided herein are methods of producing a compound of formula (D):

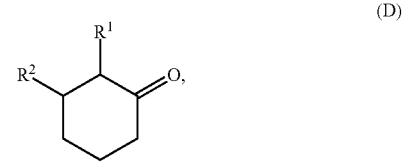

wherein $R^1$ and $R^2$ are each independently hydrogen or alkyl.

In some embodiments, the compound of formula (D) may be produced from a compound of formula (A):

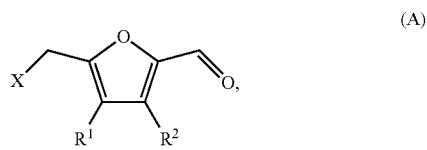

wherein:

$R^1$ and $R^2$ are as defined for formula (D) above, and

X is halo.

It should be understood that when the compound of formula (A) is used to produce the compound of formula (D), $R^1$ and $R^2$ in formulae (A) and (D) are the same.

In some variations of the compounds of formulae (A) and (D), $R^1$ and $R^2$ are both hydrogen; and the compound of formula (A) is 5-(halomethyl)furfural, and the compound of formula (D) is cyclohexanone. In other variations, $R^1$ and $R^2$ are each independently alkyl. In yet other variations, $R^1$ is hydrogen, and $R^2$ is alkyl. In any of the foregoing variations, the alkyl may be $C_{1-20}$ alkyl, $C_{1-15}$ alkyl, $C_{1-10}$ alkyl, or $C_{1-5}$ alkyl. In one variation, the alkyl may be selected from methyl, ethyl, or propyl.

Further, it should generally be understood that each $R^1$ and $R^2$ of formulae (A) and (D) as described herein may be combined as if each and every variation was individually listed.

In some embodiments, the method of producing a compound of formula (D) from a compound of formula (A) includes:

converting the compound of formula (A) to a compound of formula (B), wherein:

the compound of formula (B) is:

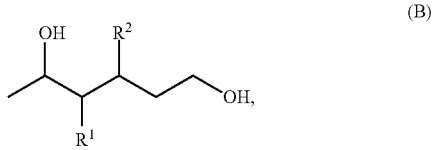

wherein $R^1$ and $R^2$ are as defined for formula (D) above;

oxidizing the compound of formula (B) to a compound of formula (C), wherein:

the compound of formula (C) is:

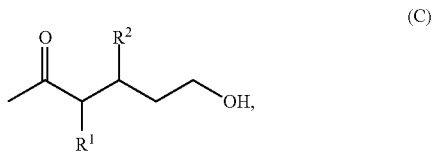

wherein $R^1$ and $R^2$ are as defined for formula (D) above; and cyclizing the compound of formula (C) to produce the compound of formula (D).

It should be understood that when the compound of formula (B) and the compound of formula (C) are produced from the compound of formula (A) and/or used in the production of the compound of formula (D), $R^1$ and $R^2$ for formulae (A), (B), (C) and (D) are the same. Further, it should generally be understood that variations of $R^1$ and $R^2$ for formulae (A) and (D) detailed throughout apply equally to formulae (B) and (C), the same as if each and every variation was specifically and individually listed for formulae (B) and (C).

For example, in one variation, $R^1$ and $R^2$ are both hydrogen, and with reference to FIG. 1, process 100 is an exemplary scheme for producing cyclohexanone 108 from 5-(halomethyl)furfural 102. In certain embodiments, the 5-(halomethyl)furfural may be 5-(chloromethyl)furfural, wherein X is chloro; or 5-(bromomethyl)furfural, wherein X is bromo. 5-(Halomethyl)furfural 102 is reduced to form hexane-1,5-diol 104. For example, the reduction may be performed in the presence of hydrogen and a catalyst, such as a metal catalyst. In certain embodiments, the metal catalyst may be a palladium catalyst.

Without wishing to be bound by any theory, 5-(halomethyl)furfural 102 may be converted into an intermediate, (5-methyltetrahydrofuran-2-yl)methanol, which is in turn converted to hexane-1,5-diol 104. In one variation, this intermediate may be isolated before further conversion into hexane-1,5-diol 104. In another variation, the reduction and ring opening to form hexane-1,5-diol 104 from 5-(halomethyl)furfural 102 may be performed without isolating this intermediate.

With reference again to FIG. 1, hexane-1,5-diol 104 is then selectively oxidized to form 6-hydroxyhexan-2-one 106. For example, the secondary alcohol of hexane-1,5-diol 104 may be selectively oxidized to a ketone via Oppenauer oxidation. 6-Hydroxyhexan-2-one 106 is then cyclized to form cyclohexanone 108. In certain embodiments, 6-hydroxyhexan-2-one 106 may be cyclized to form cyclohexanone 108 under acidic conditions, for example, in the presence of a Lewis acid. One example of a Lewis acid that may be used is zinc halide ($ZnX_2$) and an acid (HX), where X, in certain variations, may be chloro or bromo.

Without wishing to be bound by any theory, 6-hydroxyhexan-2-one 106 may be converted into an intermediate, 6-halohex-1-en-2-ol, which is in turn converted to cyclohexanone 108. In one variation, this intermediate may be isolated before further conversion into cyclohexanone 108. In another variation, the cyclizing to form cyclohexanone 108 from 6-hydroxyhexan-2-one 106 may be performed without isolating this intermediate.

It should generally be understood that the conditions described throughout with respect to exemplary process 100 (FIG. 1) may also apply to the method of producing the compound of formula (D) from the compound of formula (A).

Methods of Producing Compounds of Formula (F), Including, e.g., Hexanediol

In some aspects, provided herein are methods of producing a compound of formula (F):

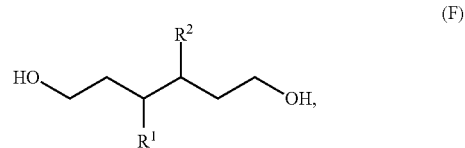

wherein $R^1$ and $R^2$ are each independently hydrogen or alkyl.

In some embodiments, the compound of formula (F) may be produced from a compound of formula (A):

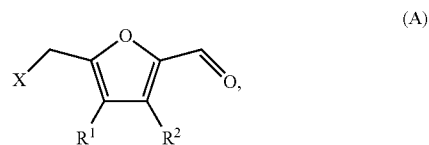

wherein:

$R^1$ and $R^2$ are as defined for formula (F) above, and

X is halo.

It should be understood that when the compound of formula (A) is used to produce the compound of formula (F), $R^1$ and $R^2$ in formulae (A) and (F) are the same.

In some variations of the compound of formulae (A) and (F), $R^1$ and $R^2$ are both hydrogen; and the compound of formula (A) is 5-(halomethyl)furfural, and the compound of formula (D) is hexane-1,6-diol. In other variations, $R^1$ and $R^2$ are each independently alkyl. In yet other variations, $R^1$ is hydrogen, and $R^2$ is alkyl. In any of the foregoing variations, the alkyl may be $C_{1-20}$ alkyl, $C_{1-15}$ alkyl, $C_{1-10}$ alkyl, or $C_{1-5}$ alkyl. In one variation, the alkyl may be selected from methyl, ethyl, or propyl.

Further, it should generally be understood that each $R^1$ and $R^2$ of formulae (A) and (F) as described herein may be combined as if each and every variation was individually listed.

In some embodiments, the method of producing a compound of formula (F) from a compound of formula (A) includes:

combining a compound of formula (A) with an alkanolate or acetate salt to produce a compound of formula (E), wherein:

the compound of formula (E) is:

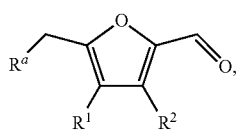

wherein:
R¹ and R² are as defined for formula (F) above, and
$R^a$ is O(alkyl) when an alkanolate salt is used, and $R^a$ is $CO_2$(alkyl) when an acetate salt is used; and
reducing the compound of formula (E) to produce the compound of formula (F).

In certain embodiments of the method, an alkanolate salt is used. It should generally be understood that alkanolate may also be known in the art as alkoxide, and an alkanolate salt may also be known in the art as an alkoxide salt. In some variations, the alkanolate salt is made up of an s block element and O(alkyl). In certain variations, the s block element may be an alkali metal or alkaline earth metal. In one variation, the alkanolate salt is $R^xR^a$, wherein $R^x$ is an alkali metal, and $R^a$ is O(alkyl). It should be understood that the connection of O(alkyl) to the parent structure is through the oxygen atom.

In other embodiments of the method, an acetate salt is used. In some variations, the acetate salt is made up of an s block element and $CO_2$(alkyl). In certain variations, the s block element may be an alkali metal or alkaline earth metal. In one variation, the acetate salt is $R^xR^a$, wherein $R^x$ is an alkali metal, and $R^a$ is $CO_2$(alkyl). It should be understood that the connection of $CO_2$(alkyl) to the parent structure is through the oxygen atom.

In certain variations of the foregoing, the alkyl of $R^a$ may be $C_{1-20}$ alkyl, $C_{1-15}$ alkyl, $C_{1-10}$ alkyl, or $C_{1-5}$ alkyl. In one variation, the alkyl of $R^a$ may be selected from methyl, ethyl, or propyl.

It should be understood that when the compound of formula (E) is produced from the compound of formula (A) and/or used in the production of the compound of formula (F), R¹ and R² for formulae (A), (E) and (F) are the same. Further, it should generally be understood that variations of R¹ and R² for formulae (A) and (F) detailed throughout apply equally to formula (E), the same as if each and every variation was specifically and individually listed for formulae (E).

Figure 2:
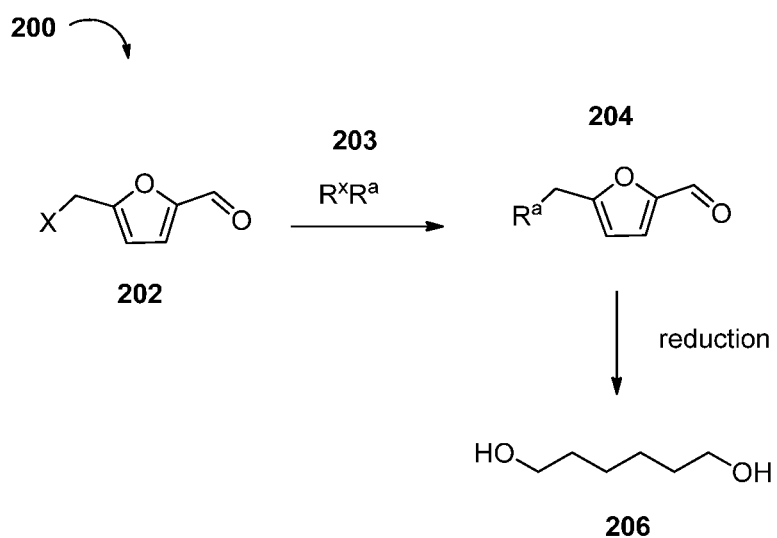
FIG. 2 depicts an exemplary scheme to produce 1,6-hexanediol from 5-(halomethyl)furfural.

For example, in one variation, R¹ and R² are both hydrogen, and with reference to FIG. 2, process 200 is an exemplary scheme for producing hexane-1,6-diol 206 from 5-(halomethyl)furfural 202. In certain embodiments, the 5-(halomethyl)furfural may be 5-(chloromethyl)furfural, wherein X is chloro; or 5-(bromomethyl)furfural, wherein X is bromo. 5-(Halomethyl)furfural 202 is contacted with a salt of formula $R^xR^a$ to produce 5-(alkoxymethyl)furan-2-carbaldehyde 204.

The salt may be an alkanolate salt, where $R^a$ is O(alkyl); or an acetate salt, where $R^a$ is COO(alkyl). In one variation, the alkyl of $R^a$ is methyl, ethyl, propyl or butyl. In certain embodiments, $R^x$ is sodium.

The 5-(alkoxymethyl)furan-2-carbaldehyde 204 is then reduced to produce hexane-1,6-diol 206. Without wishing to be bound by any theory, the 5-(alkoxymethyl)furan-2-carbaldehyde 204 may be converted into one or more intermediates. For example, the 5-(alkoxymethyl)furan-2-carbaldehyde 204 may be converted into (5-(alkoxymethyl)tetrahydrofuran-2-yl)methanol, which may in turn be converted to hexane-1,6-diol 206. The (5-(alkoxymethyl)tetrahydrofuran-2-yl)methanol may also be converted into 6-alkoxyhexanediol, such as 6-alkoxyhexane-1,1-diol and 6-alkoxyhexane-1,5-diol; and hexanetriol, such as hexane-1,1,6-triol. In certain variations, one or more of these intermediates may be isolated before further conversion into hexane-1,6-diol 206. In another variation, the reduction of 5-(alkoxymethyl)furan-2-carbaldehyde 204 to hexane-1,6-diol 206 may be performed without isolating any of these intermediates.

It should generally be understood that the conditions described throughout with respect to exemplary process 200 (FIG. 2) may also apply to the method of producing the compound of formula (F) from the compound of formula (A), including, for example, via the compound of formula (E).

Methods of Producing Compounds of Formula (I), Including, e.g., Hexamethylenediamine In some aspects, provided herein are methods of producing a compound of formula (I):

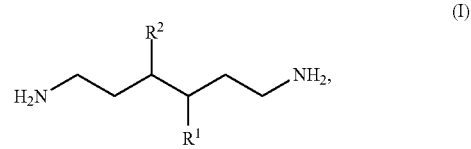

and/or a salt thereof, wherein R¹ and R² are each independently hydrogen or alkyl.

In some variations, the salt of the compound of formula (I) is a compound of formula (I-X):

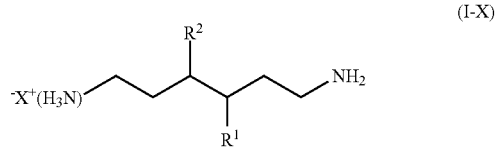

wherein X is halo.

It should generally be understood that "a compound and/or a salt thereof" may refer to (a) the compound, (b) a mixture of the compound and its salt, (c) or the salt of the compound. For example, a compound of formula (I) is produced. In other variations, a mixture of the compound of formula (I) and its salt is produced. In yet other variations, the salt of the compound of formula (I), such as a compound of formula (I-X), is produced.

In some embodiments, the compound of formula (I) and/or a salt thereof may be produced from a compound of formula (A):

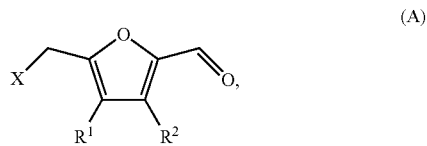

wherein:

$R^1$ and $R^2$ are as defined for formula (I) above, and

X is halo.

It should be understood that when the compound of formula (A) is used to produce the compound of formula (I) and/or a salt thereof, $R^1$ and $R^2$ in formulae (A) and (I) are the same.

In some variations of the compound of formulae (A) and (I), including any salts of the compound of formula (I), $R^1$ and $R^2$ are both hydrogen; and the compound of formula (A) is 5-(halomethyl)furfural, and the compound of formula (I) is hexamethylenediamine. In other variations, $R^1$ and $R^2$ are each independently alkyl. In yet other variations, $R^1$ is hydrogen, and $R^2$ is alkyl. In any of the foregoing variations, the alkyl may be $C_{1-20}$ alkyl, $C_{1-15}$ alkyl, $C_{1-10}$ alkyl, or $C_{1-5}$ alkyl. In one variation, the alkyl may be selected from methyl, ethyl, or propyl.

Further, it should generally be understood that each $R^1$ and $R^2$ of formulae (A) and (I) as described herein may be combined as if each and every variation was individually listed.

In some embodiments, the method of producing a compound of formula (I) from a compound of formula (A) includes:

converting a compound of formula (A) to a compound of formula (H) and/or a salt thereof, wherein:

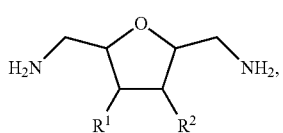

(H)

wherein $R^1$ and $R^2$ are as defined for formula (I) above; and converting the compound of formula (H) to the compound of formula (I).

In some variations, the salt of the compound of formula (H) is a compound of formula (H-X):

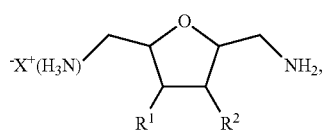

(H-X)

wherein:

$R^1$ and $R^2$ are as defined for formula (I) above; and

X is as defined for formula (A) above.

In some variations, a compound of formula (H) is produced. In other variations, a mixture of the compound of formula (H) and its salt is produced. In yet other variations, the salt of the compound of formula (H), such as a compound of formula (H-X), is produced In certain embodiments, the converting of the compound of formula (A) to a compound of formula (H) and/or a salt thereof includes:

combining the compound of formula (A) with ammonia to produce a compound of formula (G) and/or a salt thereof:

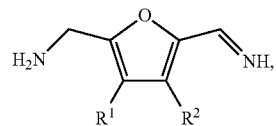

(G)

wherein $R^1$ and $R^2$ are as defined for formula (I) above; and converting the compound of formula (G) and/or a salt thereof to the compound of formula (H) and/or a salt thereof.

In some variations, the salt of the compound of formula (G) is a compound of formula (G-X):

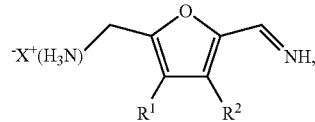

(G-X)

wherein:

$R^1$ and $R^2$ are as defined for formula (I) above; and

X is as defined for formula (A) above.

In some variations, a compound of formula (G) is produced. In other variations, a mixture of the compound of formula (G) and its salt is produced. In yet other variations, the salt of the compound of formula (G), such as a compound of formula (G-X), is produced.

In one embodiment, the compound of formula (A) and the ammonia are further combined with a metal catalyst to produce the compound of formula (G) and/or a salt thereof. In some variations, the metal catalyst is a copper catalyst. In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In other embodiments, the converting of the compound of formula (A) to a compound of formula (H) includes:

converting the compound of formula (A) to a compound of formula (L):

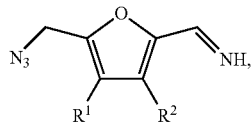

(L)

wherein $R^1$ and $R^2$ are as defined for formula (I) above; and converting the compound of formula (L) to the compound of formula (H).

In certain embodiments, the converting of the compound of formula (A) to the compound of formula (L) includes:

combining the compound of formula (A) with an azide to produce a compound of formula (K):

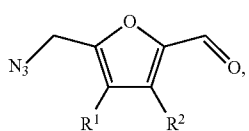

(K)

wherein R¹ and R² are as defined for formula (I) above; and combining the compound of formula (K) with ammonia to produce the compound of formula (L).

In some variations, the azide is an alkali metal azide. Suitable examples of azides that may be used include sodium azide.

In some variations, the ammonia is liquid ammonia. In other variations, the ammonia is gaseous ammonia. In certain variations, the ammonia may be produced in situ using any suitable methods known in the art. In other variations, ammonia in a solvent can be used by bubbling gaseous ammonia in a solvent.

It should be understood that when the compounds of formulae (G), (G-X), (H), (H-X), (K) and (L) are produced from the compound of formula (A) and/or used in the production of the compound of formulae (I) and (I-X), R¹ and R² for formula (A) are the same as for formulae (G), (G-X), (H), (H-X), (K) and (L). Further, it should generally be understood that variations of R¹ and R² for formulae (A), (I) and (I-X) detailed throughout apply equally to formulae (G), (G-X), (H), (H-X), (K) and (L), the same as if each and every variation was specifically and individually listed for formulae (G), (G-X), (H), (H-X), (K) and (L).

Figure 3A:
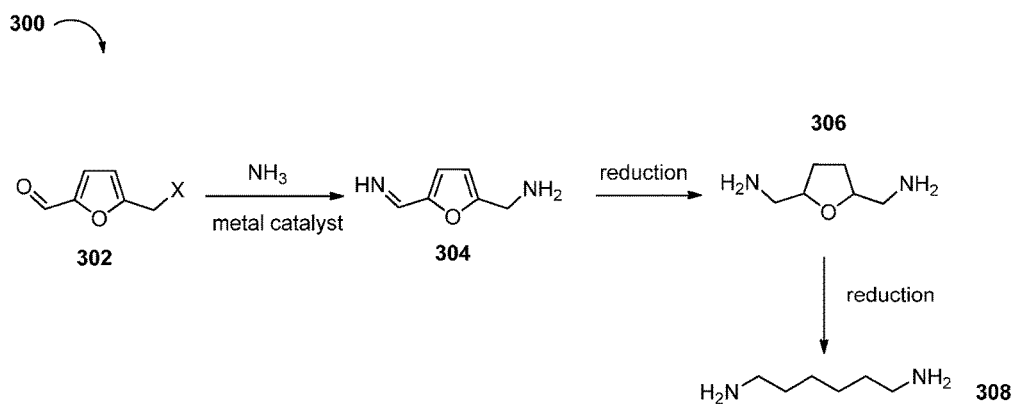
FIG. 3A, FIG. 3B, FIG. 3C, and FIG. 4 depict exemplary schemes to produce hexamethylenediamine from 5-(halomethyl)furfural.

For example, in one variation, R¹ and R² are both hydrogen, and with reference to FIG. 3A, process 300 is an exemplary scheme for producing hexamethylenediamine 306 from 5-(halomethyl)furfural 302. It should be understood that hexamethylenediamine may also be referred to as hexane-1,6-diamine or 1,6-hexanediamine. In certain embodiments, the 5-(halomethyl)furfural may be 5-(chloromethyl)furfural, wherein X is chloro; or 5-(bromomethyl)furfural, wherein X is bromo. 5-(Halomethyl)furfural 302 undergoes amination to produce (5-(iminomethyl)furan-2-yl)methanamine 304, which can be reduced to form (tetrahydrofuran-2,5-diyl)dimethanamine 306. It should be understood that the conversion of compound 302 to compound 304 may be performed, in certain embodiments, in the presence of a catalyst. In some variations, the catalyst is a metal catalyst. For example, in one variation, the catalyst is a copper catalyst. It should further be understood that in certain variations, the (5-(iminomethyl)furan-2-yl)methanamine may be isolated before reduction into (tetrahydrofuran-2,5-diyl)dimethanamine 304.

With reference again to FIG. 3A, (tetrahydrofuran-2,5-diyl)dimethanamine 304 is reduced to hexamethylenediamine 306. Without wishing to be bound by any theory, (tetrahydrofuran-2,5-diyl)dimethanamine 304 may first be converted to an intermediate, 1,6-diaminohexan-1-ol. In one variation, this intermediate may be isolated before conversion into hexamethylenediamine 306. In another variation, the conversion of the 1,6-diaminohexan-1-ol to hexamethylenediamine 306 may be performed without isolating the intermediate.

Figure 4:
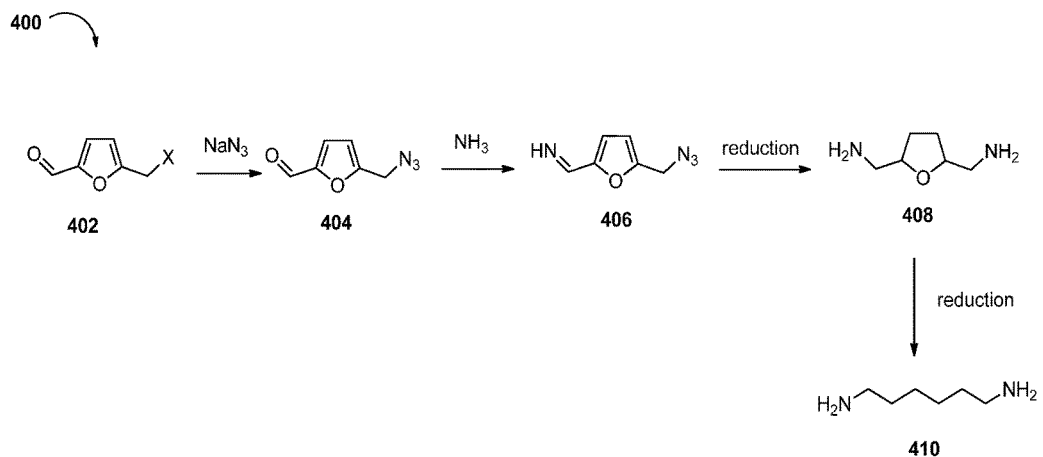

For example, in one variation, R¹ and R² are both hydrogen, and with reference to FIG. 4, hexamethylenediamine may be produced from 5-(halomethyl)furfural according to exemplary process 400. 5-(Halomethyl)furfural 402 is converted to 5-(azidomethyl)furan-2-carbaldehyde 404, which is in turn converted to (5-(azidomethyl)furan-2-yl)methanimine 406. (5-(Azidomethyl)furan-2-yl)methanimine 406 can be reduced to (tetrahydrofuran-2,5-diyl)dimethanamine 408, which is then reduced to hexamethylenediamine 410 according to the process described in process 300 (FIG. 3A) above.

It should generally be understood that the conditions described throughout with respect to exemplary process 300 (FIG. 3A) may also apply to the method of producing the compound of formula (I) from the compound of formula (A), including, for example, via the compounds of formulae (G) and (H) or via the compounds of formula (K), (L) and (H).

In other aspects, the method of producing a compound of formula (I) and/or a salt thereof from a compound of formula (A) involves the production of a compound of formula (J):

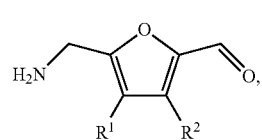

(J)

and/or a salt thereof, wherein R¹ and R² are as defined for formula (I) above.

In some embodiments, the method of producing the compound of formula (J) and/or a salt thereof from the compound of formula (A) includes:

combining the compound of formula (A) with ammonia to form a reaction mixture; and producing the compound of formula (J) and/or a salt thereof from at least a portion of the reaction mixture.

In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In some variations, the salt of the compound of formula (J) is a compound of formula (J-X):

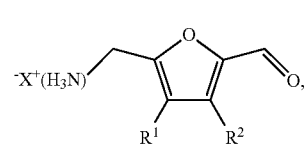

(J-X)

wherein:

R¹ and R² are as defined for formula (J) above, and

X is as defined for formula (A) above.

In some variations, a compound of formula (J) is produced. In other variations, a mixture of the compound of formula (J) and its salt is produced. In yet other variations, the salt of the compound of formula (J), such as a compound of formula (J-X), is produced.

In other aspects, provided is a method of producing a compound of formula (J-X):

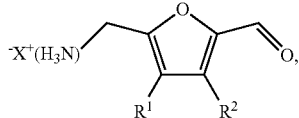

wherein:
R$^1$ and R$^2$ are each independently hydrogen or alkyl, and X is halo,
by:
combining a compound of formula (A), as described herein, with ammonia and acid to form a reaction mixture; and
producing the compound of formula (J-X) from at least a portion of the reaction mixture.

In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In some variations, the acid is HY, wherein Y is halo. In other variations, the acid is a Bronsted acid. In certain variations, the acid is a Bronsted acid with a pKa equal to or lower than 9. In one variation, the acid is sulfuric acid, phosphoric acid, trifluoroacetic acid, acetic acid, or formic acid. In another variation, the acid is sulfuric acid or phosphoric acid. Any combinations of the acids described herein may also be used.

In certain variations where the acid of HY is used, the method further includes producing a compound of formula (J-Y) from at least a portion of the reaction mixture, wherein the compound of formula (J-Y) is:

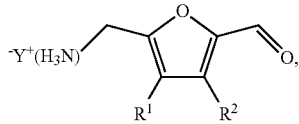

wherein:
R$^1$ and R$^2$ are as defined for formula (J-X) above, and Y is as defined for the acid.

In yet other aspects, provided is a method of producing a compound of formula (J-X):

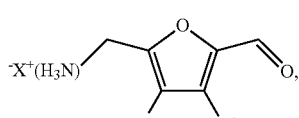

wherein:
R$^1$ and R$^2$ are each independently hydrogen or alkyl, and X is halo,
by:
a) combining a compound of formula (A), as described herein, with ammonia to form a reaction mixture;
b) producing a compound of formula (J), as described herein, in the reaction mixture; and
c) adding an acid, as described herein to the reaction mixture of step (b) to produce the compound of formula (J-X).

In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In some variations where the acid added is HY, the adding of the acid to the reaction mixture of step (b) produces the compound of formula (J-X), or a compound of formula (J-Y), as described herein, or a combination thereof.

In yet other aspects, provided is a method of producing a compound of formula (J-X):

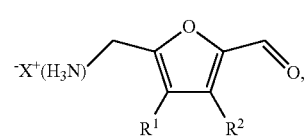

wherein:
R$^1$ and R$^2$ are each independently hydrogen or alkyl, and X is halo,
by:
a) combining a compound of formula (A), as described herein, with ammonia to form a reaction mixture;
b) producing a compound of formula (J), as described herein, from at least a portion of the reaction mixture;
c) isolating the compound of formula (J) produced; and
d) combining the isolated compound of formula (J) with an acid to produce the compound of formula (J-X).

In some variations, the combining of the isolated compound of formula (J) with the acid produces the compound of formula (J-X), or a compound of formula (J-Y), as described herein, or a combination thereof.

In other variations, the compound of formula (A) and the ammonia are further combined with a metal catalyst to form the reaction mixture. In some variation, the metal catalyst is a copper catalyst. Suitable examples of copper catalysts include copper sulfate.

In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In yet other aspects, provided is a method of producing a compound of formula (I):

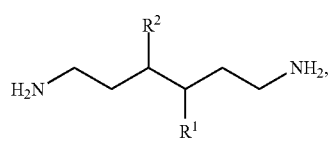

and/or a salt thereof, wherein R$^1$ and R$^2$ are each independently hydrogen or alkyl, by:
combining a compound of formula (A), as described herein, with ammonia to produce a compound of formula (J) and/or a salt thereof, as described herein;

reducing the compound of formula (J) and/or a salt thereof in the presence of ammonia to produce the compound of formula (H) and/or a salt thereof, as described herein; and further reducing the compound of formula (H) and/or a salt thereof to produce the compound of formula (I) and/or a salt thereof.

In some variations, the salt of the compound of formula (J) is a compound of formula (J-X), and the salt of the compound of formula (H) is a compound of formula (H-X):

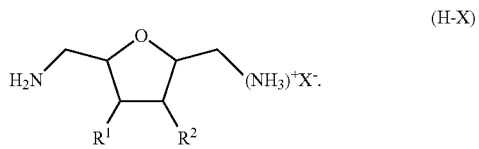

(H-X)

In some embodiments, the compound of formula (H) and/or a salt thereof may be isolated, before further reduction to produce the compound of formula (I) and/or a salt thereof.

In some variations, the compound of formula (J) and/or a salt thereof is reduced in the presence of additional ammonia, hydrogen and a catalyst to produce the compound of formula (H) of a salt thereof. In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In one variation, the catalyst may be a palladium catalyst, a platinum catalyst, or a nickel catalyst. Suitable catalysts may include, for example, Pd/C, Pt/C or Raney nickel.

In other variations, the compound of formula (H) and/or a salt thereof is further reduced in the presence of additional hydrogen and additional catalyst. In one variation, the additional catalyst is a rhodium-rhenium catalyst. Suitable catalysts include, for example, Rh—Re/SiO$_2$.

In yet other aspects, provided is a method of producing a compound of formula (I):

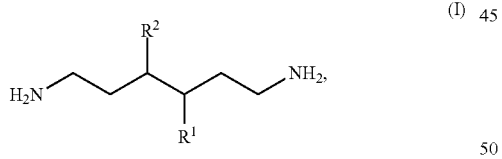

(I)

and/or a salt thereof, wherein R$^1$ and R$^2$ are each independently hydrogen or alkyl, by:

combining a compound of formula (A), as described herein, with ammonia and an acid to produce a compound of formula (J) and/or a salt thereof, as described herein;

reducing the compound of formula (J) and/or a salt thereof in the presence of ammonia to produce the compound of formula (H) and/or a salt thereof, as described herein; and further reducing the compound of formula (H) and/or a salt thereof to produce the compound of formula (I) and/or a salt thereof.

In some variations, the acid is HY, wherein Y is halo. In other variations, the acid is a Bronsted acid. In certain variations, the acid is a Bronsted acid with a pKa equal to or lower than 9. In one variation, the acid is sulfuric acid, phosphoric acid, trifluoroacetic acid, acetic acid, or formic acid. In another variation, the acid is sulfuric acid or phosphoric acid. Any combinations of the acids described herein may also be used.

In certain variations where the acid of HY is used, the method further includes producing a compound of formula (J-Y) from at least a portion of the reaction mixture, wherein the compound of formula (J-Y) is:

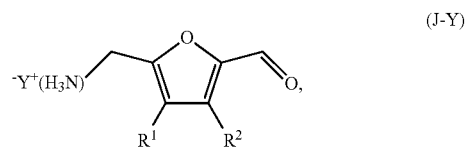

(J-Y)

wherein:
R$^1$ and R$^2$ are as defined for formula (I) above, and
Y is as defined for the acid.

In some variations, the compound of formula (J-X) is further reduced in the presence of ammonia to produce a compound of formula (H-X):

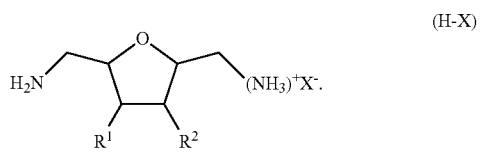

(H-X)

In other variations where the acid is HY, the compound of formula (J-Y) is produced and then further reduced in the presence of ammonia to produce a compound of formula (H-Y):

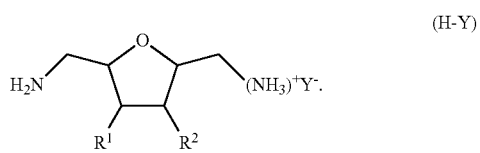

(H-Y)

It should be understood that when the compounds of formulae (J), (J-X) and (J-Y) are produced from the compound of formula (A) and/or used in the production of the compound of formula (H) and (I), R$^1$ and R$^2$ for formula (A) are the same as for formulae (G), (H), (H-X), (H-Y), (K) and (L). Further, it should generally be understood that variations of R$^1$ and R$^2$ for formulae (A) and (I) detailed throughout apply equally to formulae (G), (H), (H-X), (H-Y), (K) and (L), the same as if each and every variation was specifically and individually listed for formulae (G), (H), (H-X), (H-Y), (K) and (L).

Figure 3B:
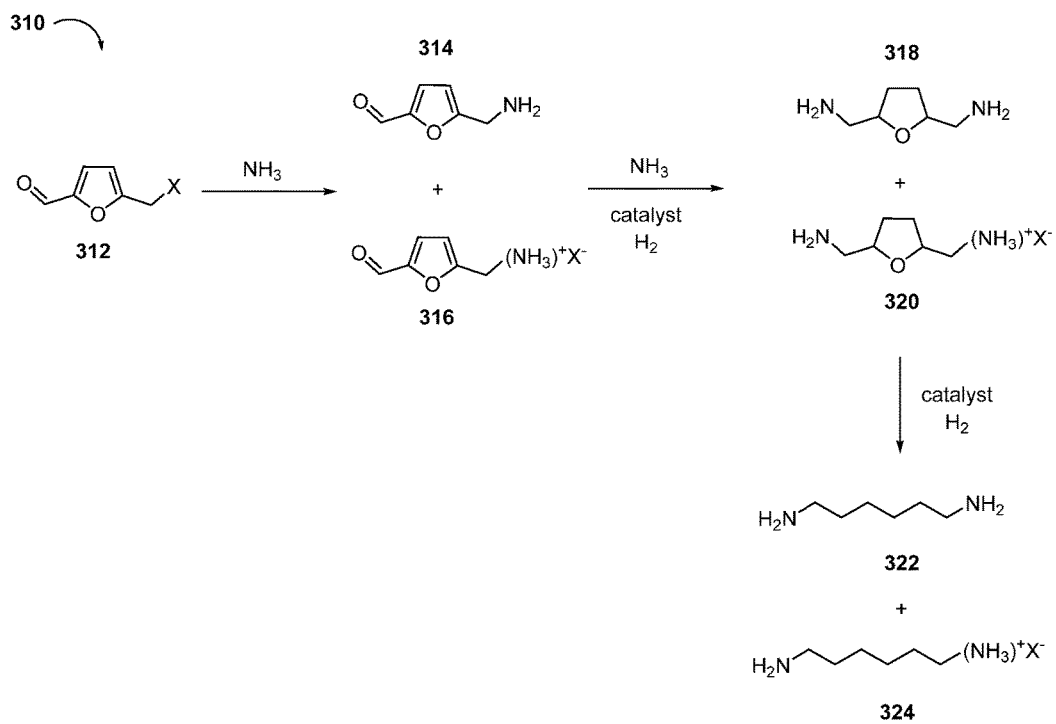

For example, in another variation, R$^1$ and R$^2$ are both hydrogen, and with reference to FIG. 3B, process 310 is another exemplary scheme for producing hexamethylenediamine from 5-(halomethyl)furfural. 5-(Halomethyl)furfural 312 may be combined with ammonia to produce 5-(aminomethyl)furan-2-carbaldehyde 314 or a halide salt thereof (compound 316). Compounds 314 and 316 can then be combined with additional ammonia, as well as hydrogen and a catalyst to produce (tetrahydrofuran-2,5-diyl)dimethanamine 318 or a halide salt thereof (compound 320). In some variations, the catalyst is a metal catalyst. In one variation, the catalyst may be a palladium catalyst, a platinum catalyst, or a nickel catalyst. Suitable catalysts may include, for example, Pd/C, Pt/C or Raney nickel.

With reference again to FIG. 3B, (tetrahydrofuran-2,5-diyl)dimethanamine 318 or a halide salt thereof (compound 320) may subsequently be further reduced to produce hexamethylenediamine 322 and/or a salt thereof (compound 324) in the presence of hydrogen and a catalyst. In some variations, the catalyst is a metal catalyst. In one variation, the catalyst may be a rhodium catalyst, a rhenium catalyst, or a rhodium/rhenium catalyst. Suitable catalysts may include, for example, Rh—Re/SiO$_2$.

Figure 3C:
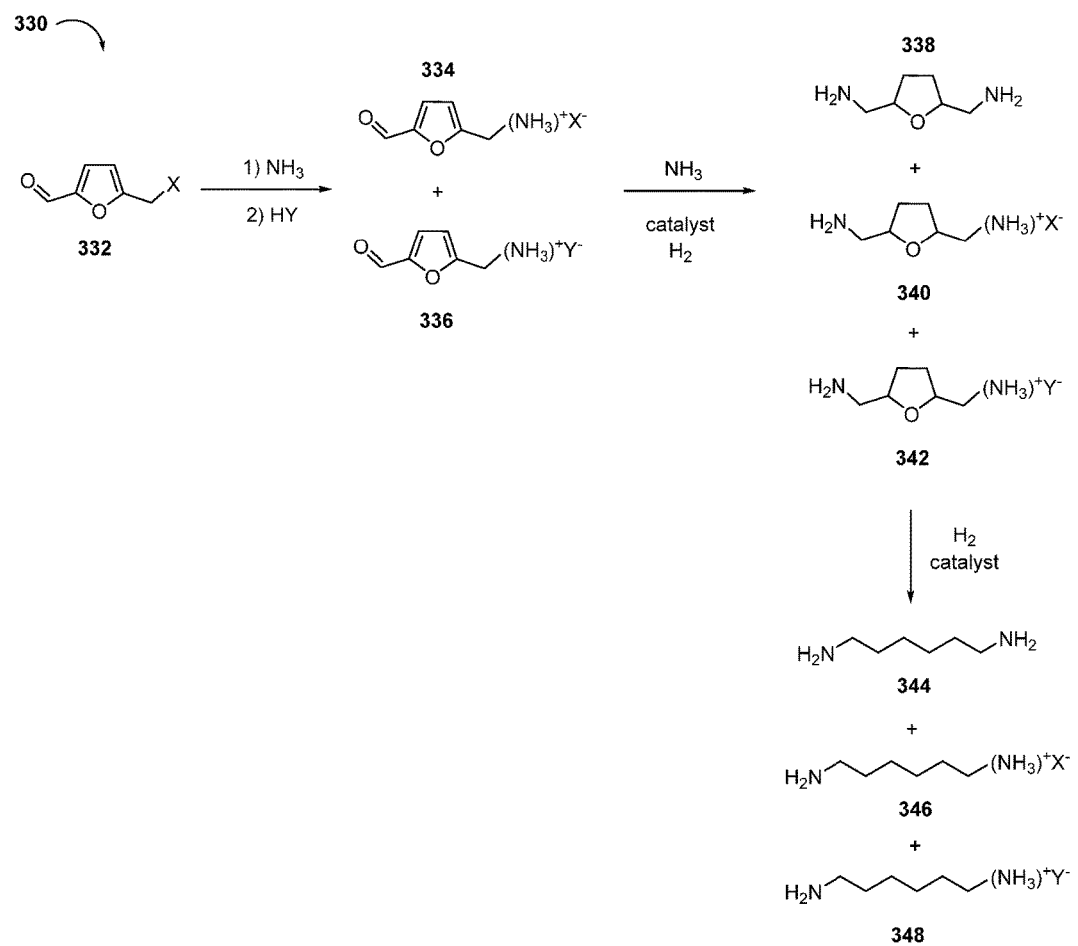

In another variation where R$^1$ and R$^2$ are both hydrogen, with reference to FIG. 3C, process 330 is yet another exemplary scheme to produce hexamethylenediamine from 5-(halomethyl)furfural. 5-(Halomethyl)furfural 332 may be combined with ammonia and acid to produce 5-(aminomethyl)furan-2-carbaldehyde 334 and a halide salt thereof (compound 336). In some variations, as depicted in FIG. 3C, the acid is HY, wherein Y is halo. When such an acid is used, a mixture of salts (compounds 334 and 336) may be obtained.

It should be understood, however, that in other variations of the method, the acid may be a Bronsted acid. In certain variations, the acid is a Bronsted acid with a pKa equal to or lower than 9. In one variation, the acid is sulfuric acid, phosphoric acid, trifluoroacetic acid, acetic acid, or formic acid. In another variation, the acid is sulfuric acid or phosphoric acid. In yet other variations, a combination of the acids described herein may also be used.

With reference again to FIG. 3C, compounds 334 and 336 can then be combined with additional ammonia, hydrogen and a catalyst to produce (tetrahydrofuran-2,5-diyl)dimethanamine 338 and halide salts thereof (compounds 340 and 342). In some variations, the catalyst is a metal catalyst. In one variation, the catalyst may be a palladium catalyst, a platinum catalyst, or a nickel catalyst. Suitable catalysts may include, for example, Pd/C, Pt/C or Raney nickel.

With reference again to FIG. 3C, (tetrahydrofuran-2,5-diyl)dimethanamine 338 and the halide salts thereof (compounds 340 and 342) may subsequently be further reduced to produce hexamethylenediamine 344 and/or salts thereof (compounds 346 and 348). In the presence of hydrogen and a catalyst. In some variations, the catalyst is a metal catalyst. In one variation, the catalyst may be a rhodium catalyst, a rhenium catalyst, or a rhodium/rhenium catalyst. Suitable catalysts may include, for example, Rh—Re/SiO$_2$.

It should further be understood that in certain variations, (tetrahydrofuran-2,5-diyl)dimethanamine 306 (FIG. 3A), 318 (FIG. 3B) and 338 (FIG. 3C) and salts thereof (where applicable) may be isolated before reduction to form the hexamethylenediamine.

It should generally be understood that the conditions described throughout with respect to exemplary process 300 (FIG. 3A), exemplary process 310 (FIG. 3B), exemplary process 330 (FIG. 3C) and exemplary process 400 (FIG. 4) may also apply to the method of producing the compounds of formulae (I) and (I-X) from the compound of formula (A), including, for example, via the compounds of formulae (G) and (G-X) and (H), (H-X) and (H-Y), or via the compounds of formulae (K), (L) and (H), or via the compounds of formula (J) and (J-X), or via the compounds of (J-X) and (J-Y).

Methods of Producing Compounds of Formula (R), Including, e.g., Caprolactam

In other aspects, provided herein are methods of producing a compound of formula (R):

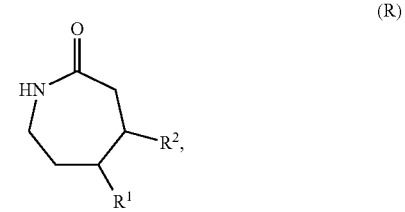

(R)

wherein R$^1$ and R$^2$ are each independently hydrogen or alkyl.

In some embodiments, the compound of formula (R) may be produced from a compound of formula (A):

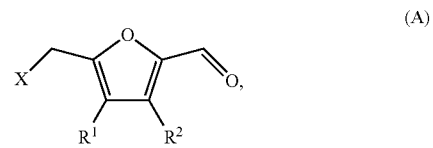

(A)

wherein:
R$^1$ and R$^2$ are as defined for formula (R) above, and
X is halo.

It should be understood that when the compound of formula (A) is used to produce the compound of formula (R), R$^1$ and R$^2$ in formulae (A) and (R) are the same.

In some variations of the compound of formulae (A) and (R), R$^1$ and R$^2$ are both hydrogen; and the compound of formula (A) is 5-(halomethyl)furfural, and the compound of formula (R) is caprolactam. In other variations, R$^1$ and R$^2$ are each independently alkyl. In yet other variations, R$^1$ is hydrogen, and R$^2$ is alkyl. In any of the foregoing variations, the alkyl may be C$_{1-20}$ alkyl, C$_{1-15}$ alkyl, C$_{1-10}$ alkyl, or C$_{1-5}$ alkyl. In one variation, the alkyl may be selected from methyl, ethyl, or propyl.

Further, it should generally be understood that each R$^1$ and R$^2$ of formulae (A) and (R) as described herein may be combined as if each and every variation was individually listed.

In some embodiments, the method of producing a compound of formula (R) from a compound of formula (A) includes:
converting the compound of formula (A) to a compound of formula (P) and/or a salt thereof:

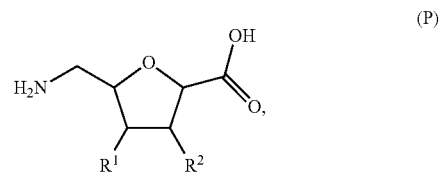

(P)

wherein R$^1$ and R$^2$ are as defined for formula (R) above; and
converting the compound of formula (P) and/or a salt thereof to the compound of formula (R).

In certain embodiments, the converting of the compound of formula (A) to the compound of formula (P) and/or a salt thereof includes:

converting the compound of formula (A) to a compound of formula (N) and/or a salt thereof:

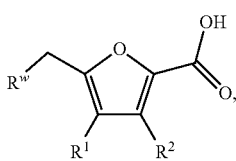

wherein:

$R^1$ and $R^2$ are as defined for formula (R) above, and $R^w$ is —NH$_2$ or —N$_3$; and reducing the compound of formula (N) to the compound of formula (P).

It should generally be understood that a salt of the compound of formula (N) may exist when $R^w$ is —NH$_2$, such that the salt is a compound of formula (N-1-X):

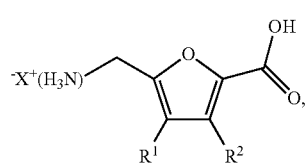

wherein X is as defined for formula (A) above.

In certain embodiments, the converting of the compound of formula (A) to the compound of formula (N) and/or a salt thereof includes:

combining the compound of formula (A) with R$^t$OH, wherein R$^t$ is an alkali metal, to produce the compound of formula (M):

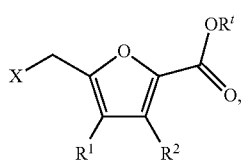

wherein R$^t$ is as defined above; and combining the compound of formula (M) with ammonia to produce the compound of formula (N) and/or a salt thereof, wherein $R^w$ is —NH$_2$.

In other embodiments, the compound of formula (A) is combined with R$^t$(OH)$_2$, wherein R$^t$ is an alkali earth metal, to produce the compound of formula (M).

In one variation, the ammonia is liquid ammonia. In another variation, the ammonia is gaseous ammonia. In certain variations, the ammonia may be produced in situ using any suitable methods known in the art. In other variations, ammonia in a solvent can be used by bubbling gaseous ammonia in a solvent.

In variations where $R^w$ is —NH$_2$, the compound of formula (N) is a compound of formula (N-1):

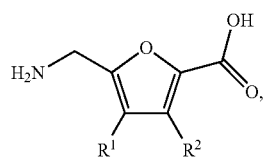

wherein $R^1$ and $R^2$ are as defined for formula (R) above.

In certain embodiments, the converting of the compound of formula (A) to the compound of formula (N) includes:

combining the compound of formula (A) with R$^t$OH, wherein R$^t$ is an alkali metal, to produce the compound of formula (M), wherein:

the compound of formula (M) is:

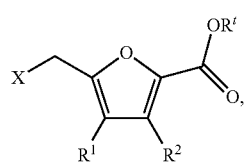

wherein R$^t$ is as defined above; and combining the compound of formula (M) with an azide to produce the compound of formula (N), wherein $R^w$ is —N$_3$.

In other embodiments, the compound of formula (A) is combined with R$^t$(OH)$_2$, wherein R$^t$ is an alkali earth metal, to produce the compound of formula (M).

In variations where $R^w$ is —N$_3$, the compound of formula (N) is a compound of formula (N-2):

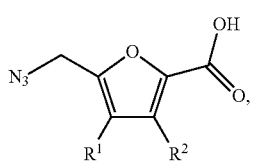

wherein $R^1$ and $R^2$ are as defined for formula (R) above.

In some variations of the foregoing embodiments, the compound of formula (A) and R$^t$OH are further combined with a metal in the presence of oxygen to produce the compound of formula (M). In certain variations, the metal is gold, palladium, platinum, or copper, or any combination thereof.

In other embodiments, the converting of the compound of formula (P) and/or a salt thereof to the compound of formula (R) includes:

converting the compound of formula (P) and/or a salt thereof to a compound of formula (Q) and/or a salt thereof:

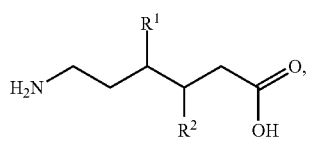

wherein R¹ and R² are as defined for formula (R) above; and cyclizing the compound of formula (Q) to produce the compound of formula (R).

In some variations, the salt of the compound of formula (Q) is a compound of formula (Q-X):

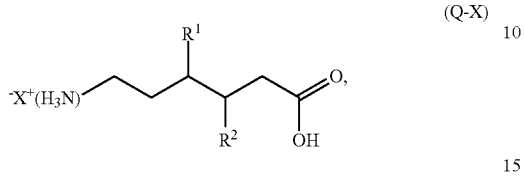

(Q-X)

wherein X is as defined for formula (A) above.

It should be understood that when the compounds of formulae (M), (N), (N-1), (N-1-X), (N-2), (P), (P-X), (Q) and (Q-X) are produced from the compound of formula (A) and/or used in the production of the compound of formula (R), R¹ and R² for formula (A) are the same as for formulae (M), (N), (N-1), (N-1-X), (N-2), (P), (P-X), (Q) and (Q-X). Further, it should generally be understood that variations of R¹ and R² for formulae (A) and (R) detailed throughout apply equally to formulae (M), (N), (N-1), (N-1-X), (N-2), (P), (P-X), (Q) and (Q-X) the same as if each and every variation was specifically and individually listed for formulae (M), (N), (N-1), (N-1-X), (N-2), (P), (P-X), (Q) and (Q-X).

Figure 5:
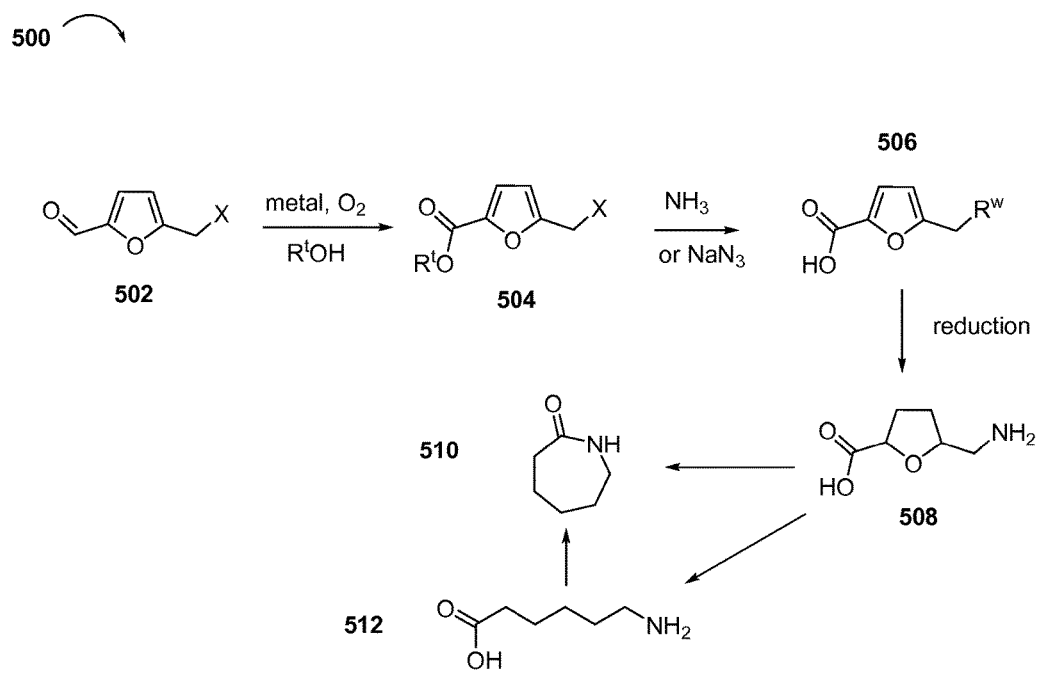
FIG. 5 depicts an exemplary scheme to produce caprolactam from 5-(halomethyl)furfural.

For example, in another variation, R¹ and R² are both hydrogen, and with reference to FIG. 5, process 500 is an exemplary scheme for producing caprolactam 510 from 5-(halomethyl)furfural 502. In certain embodiments, the 5-(halomethyl)furfural may be 5-(chloromethyl)furfural, wherein X is chloro; or 5-(bromomethyl)furfural, wherein X is bromo. 5-(Halomethyl)furfural 502 is converted to 5-(halomethyl)furan-2-carboxylate 504 in the presence of metal, oxygen and a salt. In certain embodiments, the salt has a formula R'OH, where R' is an alkali metal. In one embodiment, the salt has a formula NaOH, and compound 504 is sodium 5-(halomethyl)furan-2-carboxylate. Although not depicted in FIG. 5, it should be understood that in other variations, other salts may be used, such as a salt of formula R'(OH)₂, wherein R' is an alkali earth metal.

With reference again to FIG. 5, in one variation, 5-(halomethyl)furan-2-carboxylate 504 is contacted with NH₃ to produce 5-(aminomethyl)furan-2-carboxylic acid 506 (i.e., when R^w is NH₂). In another variation, 5-(halomethyl)furan-2-carboxylate 504 is contacted with N₃ to produce 5-(azidomethyl)furan-2-carboxylic acid 506 (i.e., when R^w is N₃). Compound 506 is then reduced to 5-(aminomethyl)tetrahydrofuran-2-carboxylic acid 508, which can then be converted to caprolactam 510.

Without wishing to be bound by any theory, 5-(aminomethyl)tetrahydrofuran-2-carboxylic acid 508 may be converted into one or more intermediates. For example, 5-(aminomethyl)tetrahydrofuran-2-carboxylic acid 508 may be converted to 6-aminohexanoic acid, which may then be converted to caprolactam 510. 5-(aminomethyl)tetrahydrofuran-2-carboxylic acid 508 may be converted to 6-amino-2-hydroxyhexanoic acid, which may then be converted into 6-aminohexanoic acid 512.

It should be understood that the conditions described throughout with respect to exemplary process 500 (FIG. 5) may also apply to the method of producing the compound of formula (R) from the compound of formula (A), including, for example, via the compounds of formulae (M), (N), (N-1), (N-1-X), (N-2), (P), (P-X), (Q) and (Q-X).

In other aspects, provided is a method of producing the compound of formula (R) by:

reducing a compound of formula (N-1) and/or a salt thereof, as described herein, to produce a compound of formula (P) and/or a salt thereof:

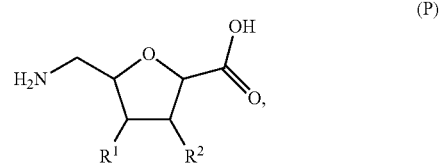

(P)

wherein R¹ and R² are as defined for formula (R) above; and converting the compound of formula (P) to the compound of formula (R).

In some embodiments, the converting of the compound of formula (P) and/or a salt thereof to the compound of formula (R) and/or a salt thereof includes:

converting the compound of formula (P) and/or a salt thereof to a compound of formula (Q) and/or a salt thereof:

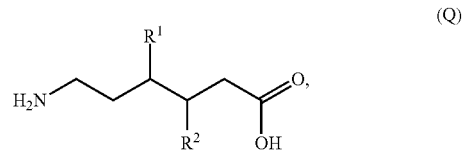

(Q)

wherein R¹ and R² are as defined for formula (R) above; and cyclizing the compound of formula (Q) to produce the compound of formula (R).

In some variations, the salt of formula (P) is a compound of formula (P-X):

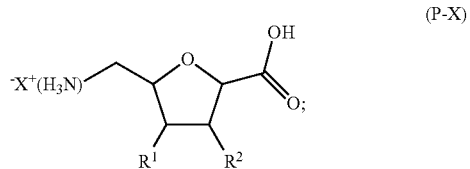

(P-X)

and the salt of formula (Q) is a compound of formula (Q-X):

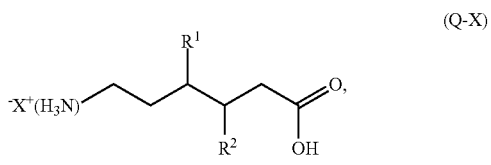

(Q-X)

In some variations, a compound of formula (P) is produced. In other variations, a mixture of the compound of formula (P) and its salt is produced. In yet other variations, the salt of the compound of formula (P), such as a compound of formula (P-X), is produced.

Similarly, in some variations, a compound of formula (Q) is produced. In other variations, a mixture of the compound of formula (Q) and its salt is produced. In yet other variations, the salt of the compound of formula (Q), such as a compound of formula (Q-X), is produced.

It should be understood that when the compounds of formulae (N), (N-1), (N-1-X), (P), (P-X), (Q) and (Q-X) are used in the production of the compound of formula (R), $R^1$ and $R^2$ for formula (R) are the same as for formulae (N), (N-1), (N-1-X), (P), (P-X), (Q) and (Q-X). Further, it should generally be understood that variations of $R^1$ and $R^2$ for formula (R) detailed throughout apply equally to formulae (N), (N-1), (N-1-X), (P), (P-X), (Q) and (Q-X) the same as if each and every variation was specifically and individually listed for formulae (N), (N-1), (N-1-X), (P), (P-X), (Q) and (Q-X).

Polymer of Formula (V), Including, e.g., Nylon, and Methods of Producing Thereof In yet other aspects, provided herein are methods of producing a polymer of formula (V):

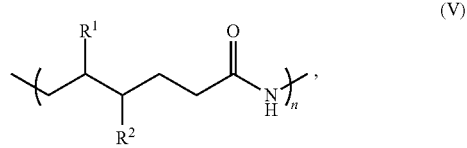

wherein:

$R^1$ and $R^2$ are each independently hydrogen or alkyl, and n is greater than 1.

In some embodiments, the polymer of formula (V) may be produced from a compound of formula (N-1) and/or a salt thereof:

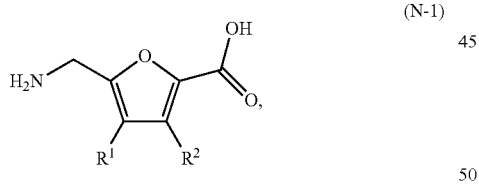

wherein $R^1$ and $R^2$ are as defined for formula (V) above.

The compound of formula (N-1) and/or a salt thereof may be produced according to any of the methods described herein, including, for example, from the compounds of formulae (A) and (M), as described herein.

Further, it should be understood that when the compound of formula (N-1) and/or a salt thereof is used to produce the polymer of formula (V), $R^1$ and $R^2$ in formulae (N-1) and (V) are the same.

In some variations of the compounds of formulae (N-1) and (V), $R^1$ and $R^2$ are both hydrogen; and the compound of formula (N-1) is 5-(aminomethyl)furan-2-carboxylic acid, and the polymer of formula (V) is nylon. In some variations, where $R^1$ and $R^2$ are both hydrogen, the polymer of formula (V) is a polymer of formula (X):

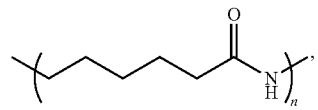

wherein n is an integer greater than 1.

In other variations, $R^1$ and $R^2$ are each independently alkyl. In yet other variations, $R^1$ is hydrogen, and $R^2$ is alkyl. In any of the foregoing variations, the alkyl may be $C_{1-20}$ alkyl, $C_{1-15}$ alkyl, $C_{1-10}$ alkyl, or $C_{1-5}$ alkyl. In one variation, the alkyl may be selected from methyl, ethyl, or propyl.

In some variations, the method of producing a polymer of formula (V) from the compound of formula (N-1) and/or a salt thereof, as described herein, includes:

polymerizing the compound of formula (N-1) and/or a salt thereof to produce a polymer of formula (T):

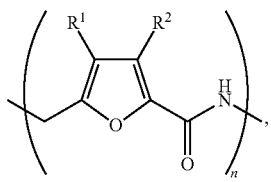

wherein $R^1$, $R^2$ and n are as defined for formula (V) above;

reducing the polymer of formula (T) to a polymer of formula (U), wherein:

the polymer of formula (U) is:

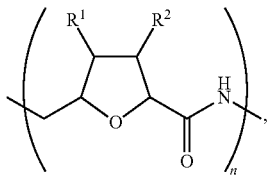

wherein $R^1$, $R^2$ and n are as defined for formula (V) above; and converting the polymer of formula (U) to the polymer of formula (V).

Figure 7:
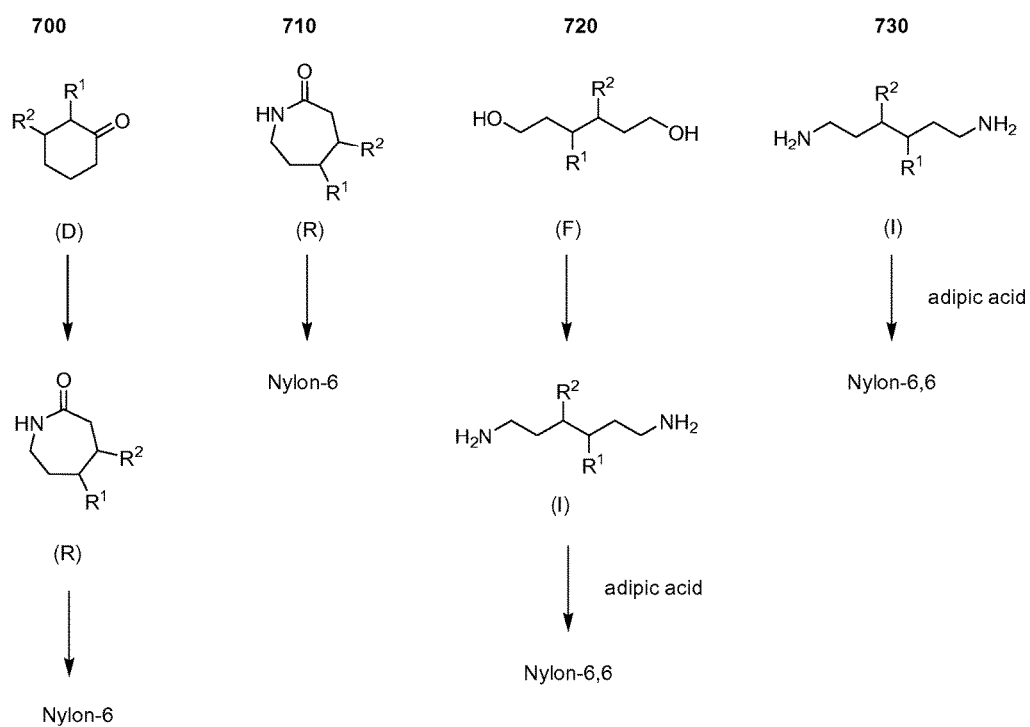
FIG. 7 depicts exemplary schemes to produce nylon.

In other embodiments, the polymer of formula (V) may be produced from a compound of formula (D), or a compound of formula (F), or a compound of formula (I), or a compound of formula (R), or any combinations thereof. Any suitable methods known in the art to convert such compounds may be used. See FIG. 7. It should be understood that when the compound of formula (D), (F), (I) or (R), or any combination thereof, is used to produce the polymer of formula (V), $R^1$ and $R^2$ in formulae (D), (F), (I) or (R), and (V) are the same.

In some variations of the compound of formula (D), (F), (I) or (R), or any combination thereof, and (V), $R^1$ and $R^2$ are both hydrogen; and the compound of formula (D) is cyclohexanone, the compound of formula (F) is hexane-1,6-diol, the compound of formula (I) is hexamethylenediamine, the compound of formula (R) is caprolactam, and the polymer of formula (V) is nylon.

Thus, in some variations, the cyclohexanone, hexane-1,6-diol, hexamethylenediamine, caprolactam, or any combination thereof, produced from 5-(halomethyl)furfural by the methods described herein may be used as precursors to produce nylon. Nylon refers to a family of aliphatic polyamides. Examples of nylon include nylon-6,6; nylon-6; nylon-6,9; nylon-6,10; nylon-6,12; nylon-11; nylon-12 and nylon-4,6. In one embodiment, the nylon is nylon-6.

In other variations, $R^1$ and $R^2$ are each independently alkyl. In yet other variations, $R^1$ is hydrogen, and $R^2$ is alkyl. In any of the foregoing variations, the alkyl may be $C_{1-20}$ alkyl, $C_{1-15}$ alkyl, $C_{1-10}$ alkyl, or $C_{1-5}$ alkyl. In one variation, the alkyl may be selected from methyl, ethyl, or propyl.

Figure 6:
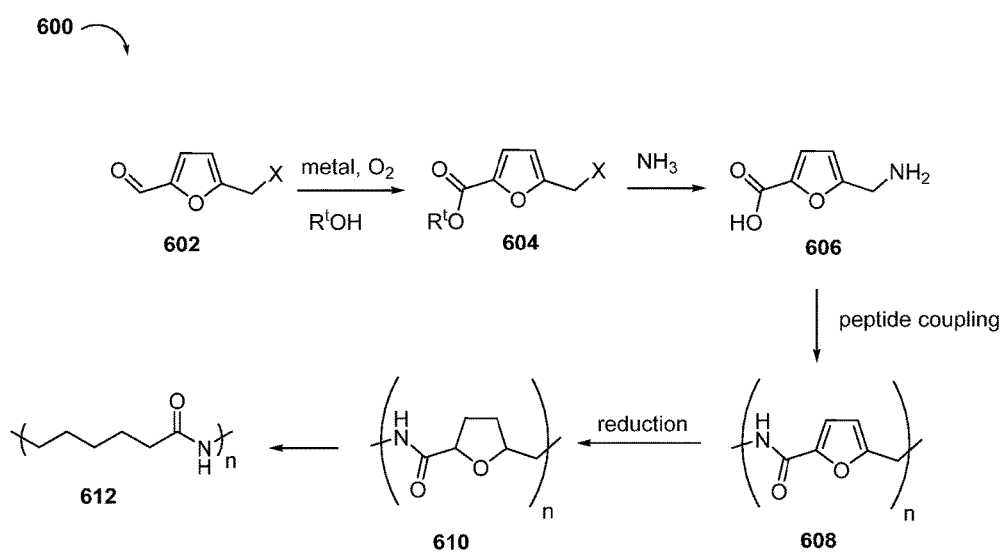
FIG. 6 depicts an exemplary scheme to produce nylon-6 from 5-(halomethyl)furfural.

Any suitable methods known in the art may be employed to produce nylon from the cyclohexanone, hexane-1,6-diol, hexamethylenediamine, or caprolactam produced from 5-(halomethyl)furfural. In one embodiment, FIG. 6 provides exemplary process 600 for producing nylon-6 from 5-(halomethyl)furfural. In certain embodiments, the 5-(halomethyl)furfural may be 5-(chloromethyl)furfural, wherein X is chloro; or 5-(bromomethyl)furfural, wherein X is bromo.

Enumerated Embodiments

The following enumerated embodiments are representative of some aspects of the invention.

1. A method of producing a compound of formula (D):

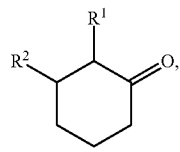

(D)

wherein $R^1$ and $R^2$ are each independently hydrogen or alkyl,
the method comprising:
converting a compound of formula (A) to a compound of formula (B), wherein:
the compound of formula (A) is:

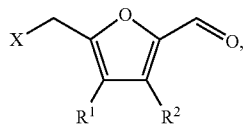

(A)

wherein:
$R^1$ and $R^2$ are as defined for formula (D) above, and
X is halo, and
the compound of formula (B) is:

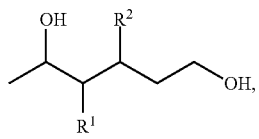

(B)

wherein $R^1$ and $R^2$ are as defined for formula (D) above;
oxidizing the compound of formula (B) to a compound of formula (C), wherein:
the compound of formula (C) is:

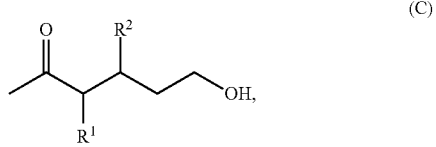

(C)

wherein $R^1$ and $R^2$ are as defined for formula (D) above; and
cyclizing the compound of formula (C) to produce the compound of formula (D).

2. The method of embodiment 1, wherein $R^1$ and $R^2$ are both hydrogen.
3. The method of embodiment 1 or 2, wherein the compound of formula (C) is cyclized to produce the compound of formula (D) in the presence of an acid.
4. The method of embodiment 3, wherein the acid is a Lewis acid.
5. A method of producing cyclohexanone, comprising:
converting 5-(halomethyl)furfural to hexane-1,5-diol;
oxidizing the hexane-1,5-diol to produce 6-hydroxyhexan-2-one; and
cyclizing the 6-hydroxyhexan-2-one to produce cyclohexanone.
6. The method of embodiment 5, wherein the 6-hydroxyhexan-2-one to is cyclized to produce the cyclohexanone in the presence of an acid.
7. The method of embodiment 6, wherein the acid is a Lewis acid.
8. A method of producing a compound of formula (F):

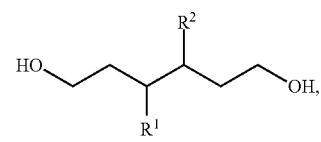

(F)

wherein $R^1$ and $R^2$ are each independently hydrogen or alkyl,
the method comprising:
combining a compound of formula (A) with an alkanolate or acetate salt to produce a compound of formula (E), wherein:
the compound of formula (A) is:

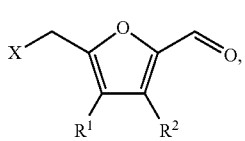

(A)

wherein:
$R^1$ and $R^2$ are as defined for formula (F) above, and
X is halo, and the compound of formula (E) is:

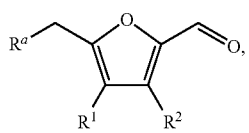
(E)

wherein:
R¹ and R² are as defined for formula (F) above, and
$R^a$ is O(alkyl) when an alkanolate salt is used, and $R^a$ is $CO_2$(alkyl) when an acetate salt is used; and
reducing the compound of formula (E) to produce the compound of formula (F).

9. The method of embodiment 8, wherein R¹ and R² are both hydrogen.

10. A method of producing hexane-1,6-diol, comprising:
contacting 5-(halomethyl)furfural with an alkanolate or acetate salt to produce 5-(alkoxymethyl)furan-2-carbaldehyde; and
reducing the 5-(alkoxymethyl)furan-2-carbaldehyde to produce hexane-1,6-diol.

11. A method of producing a compound of formula (I):

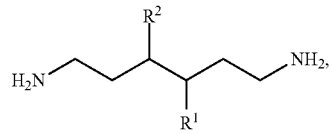
(I)

or a salt thereof, wherein R¹ and R² are each independently hydrogen or alkyl,
the method comprising:
converting a compound of formula (A) to a compound of formula (H) and/or a salt thereof, wherein:
the compound of formula (A) is:

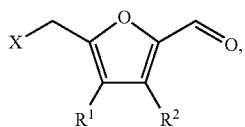
(A)

wherein:
R¹ and R² are as defined for formula (I) above, and
X is halo, and
the compound of formula (H) is:

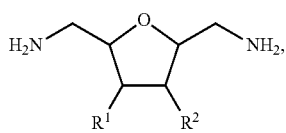
(H)

wherein R¹ and R² are as defined for formula (I) above; and
converting the compound of formula (H) and/or a salt thereof to the compound of formula (I).

12. The method of embodiment 11, wherein R¹ and R² are both hydrogen.

13. The method of embodiment 11 or 12, wherein the converting of the compound of formula (A) to a compound of formula (H) and/or a salt thereof comprises:
combining the compound of formula (A) with ammonia to produce a compound of formula (G) and/or a salt thereof, wherein:
the compound of formula (G) is:

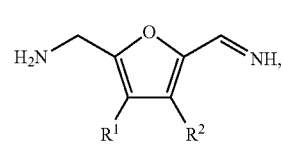
(G)

wherein R¹ and R² are as defined for formula (I) above; and
converting the compound of formula (G) and/or a salt thereof to the compound of formula (H) and/or a salt thereof.

14. The method of embodiment 13, wherein the compound of formula (A) and the ammonia are further combined with a metal catalyst to produce the compound of formula (G) and/or a salt thereof.

15. The method of embodiment 14, wherein the metal catalyst is a copper catalyst.

16. The method of embodiment 11 or 12, wherein the converting of the compound of formula (A) to a compound of formula (H) comprises:
converting the compound of formula (A) to a compound of formula (L), wherein:
the compound of formula (L) is:

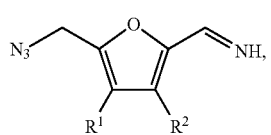
(L)

wherein R¹ and R² are as defined for formula (I) above; and
converting the compound of formula (L) to the compound of formula (H).

17. The method of embodiment 16, wherein the converting of the compound of formula (A) to the compound of formula (L) comprises:
combining the compound of formula (A) with an azide to produce a compound of formula (K), wherein:
the compound of formula (K) is:

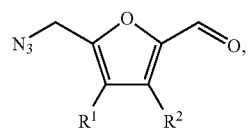
(K)

wherein R¹ and R² are as defined for formula (I) above; and
combining the compound of formula (K) with ammonia to produce the compound of formula (L).

18. A method of producing hexamethylenediamine, comprising:
converting 5-(halomethyl)furfural to (tetrahydrofuran-2,5-diyl)dimethanamine; and
converting the (tetrahydrofuran-2,5-diyl)dimethanamine to hexamethylenediamine.
19. The method of embodiment 18, wherein the converting of 5-(halomethyl)furfural to (tetrahydrofuran-2,5-diyl)dimethanamine comprises:
converting the 5-(halomethyl)furfural to (5-(iminomethyl)furan-2-yl)methanamine; and
converting the (5-(iminomethyl)furan-2-yl)methanamine to the (tetrahydrofuran-2,5-diyl)dimethanamine.
20. The method of embodiment 18, wherein the converting of 5-(halomethyl)furfural to (tetrahydrofuran-2,5-diyl)dimethanamine comprises:
combining the 5-(halomethyl)furfural with ammonia to produce (5-(iminomethyl)furan-2-yl)methanamine; and
reducing the (5-(iminomethyl)furan-2-yl)methanamine to produce the (tetrahydrofuran-2,5-diyl)dimethanamine.
21. The method of embodiment 20, wherein the 5-(halomethyl)furfural and the ammonia are further combined with a metal catalyst to produce the (5-(iminomethyl)furan-2-yl)methanamine.
22. The method of embodiment 21, wherein the metal catalyst is a copper catalyst.
23. The method of embodiment 18, wherein the converting of 5-(halomethyl)furfural to (tetrahydrofuran-2,5-diyl)dimethanamine comprises:
converting the 5-(halomethyl)furfural to (5-(azidomethyl)furan-2-yl)methanimine; and
converting the (5-(azidomethyl)furan-2-yl)methanimine to the (tetrahydrofuran-2,5-diyl)dimethanamine.
24. The method of embodiment 23, wherein the converting of the 5-(halomethyl)furfural to (5-(azidomethyl)furan-2-yl)methanimine comprises:
combining the 5-(halomethyl)furfural with an azide to produce 5-(azidomethyl)furan-2-carbaldehyde; and
combining the 5-(azidomethyl)furan-2-carbaldehyde with ammonia to produce the (5-(azidomethyl)furan-2-yl)methanimine.
25. A method of producing a compound of formula (J):

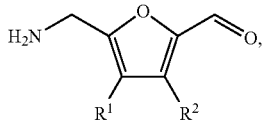

(J)

and/or a salt thereof, wherein $R^1$ and $R^2$ are each independently hydrogen or alkyl,
the method comprising:
combining a compound of formula (A) with ammonia to form a reaction mixture, wherein:
the compound of formula (A) is:

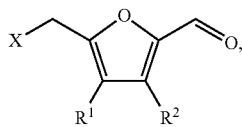

(A)

wherein:
$R^1$ and $R^2$ are as defined for formula (J) above, and
X is halo, and
producing the compound of formula (J) and/or a salt thereof from at least a portion of the reaction mixture.
26. The method of embodiment 25, wherein $R^1$ and $R^2$ are both hydrogen.
27. The method of embodiment 25 or 26, wherein the salt of the compound of formula (J) is a compound of formula (J-X):

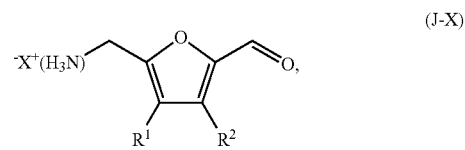

(J-X)

wherein:
$R^1$ and $R^2$ are as defined for formula (J) above, and
X is as defined for formula (A) above.
28. A method of producing a compound of formula (J-X):

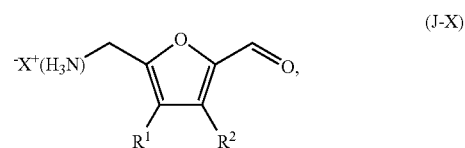

(J-X)

wherein:
$R^1$ and $R^2$ are each independently hydrogen or alkyl, and
X is halo,
the method comprising:
combining a compound of formula (A) with ammonia and acid to form a reaction mixture, wherein:
the compound of formula (A) is:

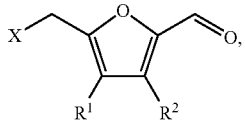

(A)

wherein:
$R^1$ and $R^2$ are as defined for formula (J-X) above, and
X is halo, and
producing the compound of formula (J-X) from at least a portion of the reaction mixture.
29. The method of embodiment 28, wherein $R^1$ and $R^2$ are both hydrogen.
30. The method of embodiment 28 or 29, wherein the acid is HY, wherein Y is halo.
31. The method of embodiment 28 or 29, wherein the acid is a Bronsted acid.
32. The method of embodiment 30, further comprising producing a compound of formula (J-Y) from at least a portion of the reaction mixture, wherein the compound of formula (J-Y) is:

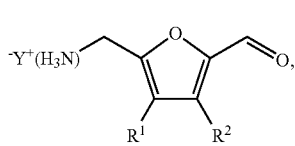

(J-Y)

wherein:
R[1] and R[2] are as defined for formula (J-X) above, and Y is as defined for the acid.

33. A method of producing a compound of formula (J-X):

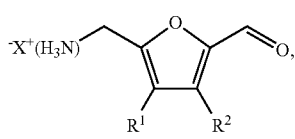

(J-X)

wherein:
R[1] and R[2] are each independently hydrogen or alkyl, and X is halo,
the method comprising:
  a) combining a compound of formula (A) with ammonia to form a reaction mixture, wherein:
    the compound of formula (A) is:

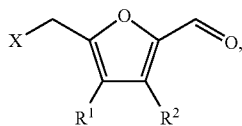

(A)

wherein:
R[1] and R[2] are as defined for formula (J-X) above, and
X is halo;
  b) producing a compound of formula (J) in the reaction mixture, wherein the compound of formula (J) is:

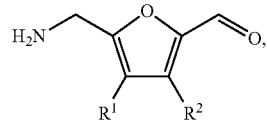

(J)

wherein R[1] and R[2] are as defined for formula (J-X) above; and
    c) adding an acid to the reaction mixture of step (b) to produce the compound of formula (J-X).

34. The method of embodiment 33, wherein R[1] and R[2] are both hydrogen.

35. The method of embodiment 33 or 34, wherein the acid is HY, wherein Y is halo.

36. The method of embodiment 33 or 34, wherein the acid is a Bronsted acid.

37. The method of embodiment 35, wherein the adding of the acid to the reaction mixture of step (b) produces the compound of formula (J-X), or a compound of formula (J-Y), or a combination thereof, wherein the compound of formula (J-Y) is:

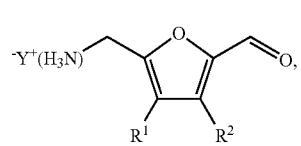

(J-Y)

wherein:
R[1] and R[2] are as defined for formula (J-X) above, and Y is as defined for the acid.

38. A method of producing a compound of formula (J-X):

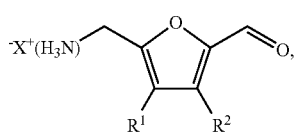

(J-X)

wherein:
R[1] and R[2] are each independently hydrogen or alkyl, and X is halo,
the method comprising:
  a) combining a compound of formula (A) with ammonia to form a reaction mixture, wherein:
    the compound of formula (A) is:

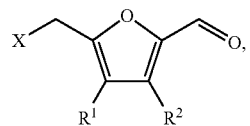

(A)

wherein:
R[1] and R[2] are as defined for formula (J-X) above, and
X is halo;
  b) producing a compound of formula (J) from at least a portion of the reaction mixture, wherein the compound of formula (J) is:

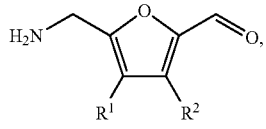

(J)

wherein R[1] and R[2] are as defined for formula (J-X) above; and
    c) isolating the compound of formula (J) produced; and
    d) combining the isolated compound of formula (J) with an acid to produce the compound of formula (J-X).

39. The method of embodiment 38, wherein R[1] and R[2] are both hydrogen.

40. The method of embodiment 38 or 39, wherein the acid is HY, wherein Y is halo.

41. The method of embodiment 38 or 39, wherein the acid is a Bronsted acid.

42. The method of any one of embodiments 38 to 40, wherein the combining of the isolated compound of formula (J) with the acid produces the compound of formula (J-X), or a compound of formula (J-Y), or a combination thereof, wherein the compound of formula (J-Y) is:

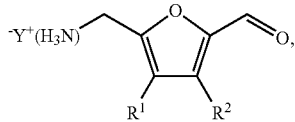
(J-Y)

wherein:
$R^1$ and $R^2$ are as defined for formula (J-X) above, and Y is as defined for the acid.
43. The method of any one of embodiments 25 to 42, wherein the compound of formula (A) and the ammonia are further combined with a metal catalyst to form the reaction mixture.
44. The method of embodiment 43, wherein the metal catalyst is a copper catalyst.
45. A method of producing a compound of formula (I):

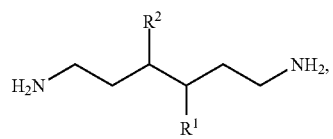
(I)

or a salt thereof, wherein $R^1$ and $R^2$ are each independently hydrogen or alkyl,
the method comprising:
  combining a compound of formula (A) with ammonia to produce a compound of formula (J) and/or a salt thereof, wherein:
    the compound of formula (A) is:

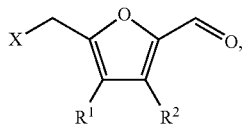
(A)

wherein:
      $R^1$ and $R^2$ are as defined for formula (I) above, and
      X is halo, and
    the compound of formula (J) is:

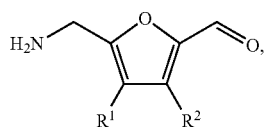
(J)

and/or a salt thereof, wherein $R^1$ and $R^2$ are as defined for formula (I) above; and
  reducing the compound of formula (J) and/or a salt thereof in the presence of additional ammonia to produce the compound of formula (H) and/or a salt thereof, wherein:

the compound of formula (H) is:

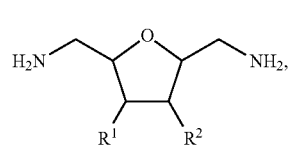
(H)

wherein $R^1$ and $R^2$ are as defined for formula (I) above; and
  further reducing the compound of formula (H) and/or a salt thereof to produce the compound of formula (I) and/or a salt thereof.
46. The method of embodiment 45, wherein $R^1$ and $R^2$ are both hydrogen.
47. The method of embodiment 45 or 46, wherein the compound of formula (J) and/or a salt thereof is reduced in the presence of the additional ammonia, hydrogen and a metal catalyst to produce the compound of formula (H) and/or a salt thereof.
48. The method of embodiment 47, wherein the metal catalyst is a palladium catalyst, a platinum catalyst, or a nickel catalyst, or any combination thereof.
49. The method of embodiment 48, wherein the metal catalyst is Pd/C, Pt/C or Raney nickel, or any combination thereof.
50. The method of any one of embodiments 45 to 49, wherein the compound of formula (H) and/or a salt thereof is further reduced in the presence of hydrogen and an additional metal catalyst.
51. The method of embodiment 50, wherein the additional metal catalyst is a rhodium catalyst, a rhenium catalyst, or a rhodium-rhenium catalyst.
52. The method of embodiment 51, wherein the additional metal catalyst is Rh—Re/SiO$_2$.
53. The method of any one of embodiments 45 to 52, wherein the compound of formula (A) and the ammonia are further combined with a metal catalyst to produce the compound of formula (J) and/or a salt thereof.
54. The method of embodiment 55, wherein the metal catalyst is a copper catalyst.
55. A method of producing a compound of formula (R):

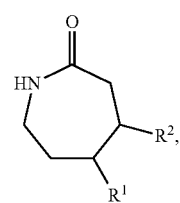
(R)

wherein $R^1$ and $R^2$ are each independently hydrogen or alkyl,
the method comprising:
  converting a compound of formula (A) to a compound of formula (P) and/or a salt thereof, wherein:
    the compound of formula (A) is:

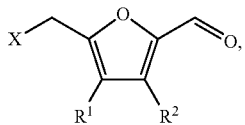
(A)

wherein:
R¹ and R² are as defined for formula (R) above, and
X is halo, and
the compound of formula (P) is:

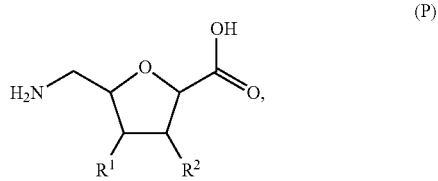

wherein R¹ and R² are as defined for formula (R) above; and
converting the compound of formula (P) and/or a salt thereof to the compound of formula (R).

56. The method of embodiment 55, wherein R¹ and R² are both hydrogen.

57. The method of embodiment 55 or 56, wherein the converting of the compound of formula (A) to the compound of formula (P) and/or a salt thereof comprises:
converting the compound of formula (A) to a compound of formula (N) and/or a salt thereof, wherein:
the compound of formula (N) is:

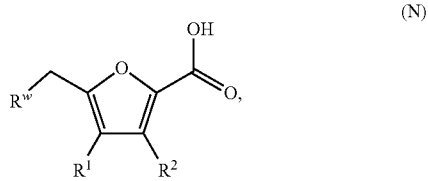

wherein:
R¹ and R² are as defined for formula (R) above, and
$R^w$ is —NH$_2$ or —N$_3$; and
reducing the compound of formula (N) and/or a salt thereof to the compound of formula (P) and/or a salt thereof.

58. The method of embodiment 57, wherein the converting of the compound of formula (A) to the compound of formula (N) and/or a salt thereof comprises:
combining the compound of formula (A) with R'OH, wherein R' is an alkali metal, to produce the compound of formula (M), wherein:
the compound of formula (M) is:

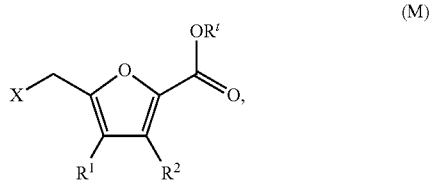

wherein R' is as defined above; and
combining the compound of formula (M) with ammonia to produce the compound of formula (N) and/or a salt thereof, wherein $R^w$ is —NH$_2$.

59. The method of embodiment 57, wherein the converting of the compound of formula (A) to the compound of formula (N) comprises:
combining the compound of formula (A) with R'OH, wherein R' is an alkali metal, to produce the compound of formula (M), wherein:
the compound of formula (M) is:

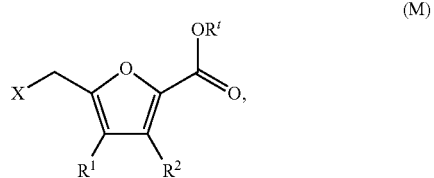

wherein R' is as defined above; and
combining the compound of formula (M) with an azide to produce the compound of formula (N), wherein $R^w$ is —N$_3$.

60. The method of embodiment 55 or 59, wherein the compound of formula (A) and R'OH are further combined with a metal in the presence of oxygen to produce the compound of formula (M).

61. The method of any one of embodiments 55 to 60, wherein the converting of the compound of formula (P) and/or a salt thereof to the compound of formula (R) and/or a salt thereof comprises:
converting the compound of formula (P) and/or a salt thereof to a compound of formula (Q) and/or a salt thereof, wherein:
the compound of formula (Q) is:

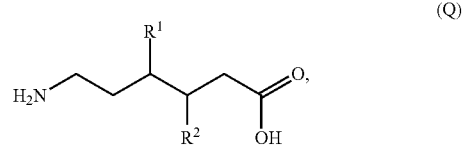

wherein R¹ and R² are as defined for formula (R) above; and
cyclizing the compound of formula (Q) and/or a salt thereof to produce the compound of formula (R).

62. A method for producing caprolactam, comprising:
converting 5-(halomethyl)furfural to 5-(aminomethyl)tetrahydrofuran-2-carboxylic acid; and
converting the 5-(aminomethyl)tetrahydrofuran-2-carboxylic acid to caprolactam.

63. A method of producing a compound of formula (R):

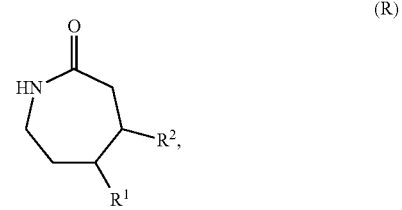

wherein R¹ and R² are each independently hydrogen or alkyl, the method comprising:

reducing a compound of formula (N-1) and/or a salt thereof to produce a compound of formula (P) and/or a salt thereof, wherein:

the compound of formula (N-1) is:

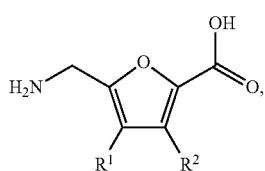

(N-1)

wherein $R^1$ and $R^2$ are as defined for formula (R) above, and the compound of formula (P) is:

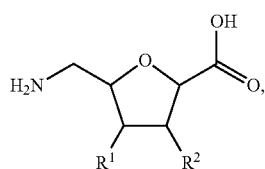

(P)

wherein $R^1$ and $R^2$ are as defined for formula (R) above; and converting the compound of formula (P) and/or salt thereof to the compound of formula (R).

64. The method of embodiment 63, wherein $R^1$ and $R^2$ are both hydrogen.

65. The method of embodiment 63 or 64, wherein the compound of formula (N-1) and/or a salt thereof is produced according to the method of any one of embodiments 54 to 57.

66. The method of any one of embodiments 63 to 65, wherein the converting of the compound of formula (P) and/or a salt thereof to the compound of formula (R) comprises:

converting the compound of formula (P) and/or a salt thereof to a compound of formula (Q) and/or a salt thereof, wherein:

the compound of formula (Q) is:

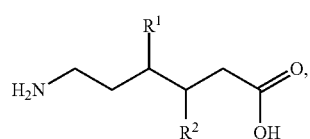

(Q)

wherein $R^1$ and $R^2$ are as defined for formula (R) above; and cyclizing the compound of formula (Q) and/or a salt thereof to produce the compound of formula (R).

67. A method of producing a polymer of formula (V):

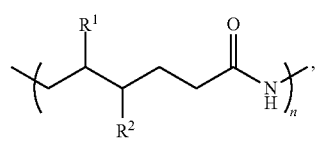

(V)

wherein:

$R^1$ and $R^2$ are each independently hydrogen or alkyl, and n is greater than 1, the method comprising:

polymerizing a compound of formula (N-1) and/or a salt thereof to produce a polymer of formula (T), wherein:

the compound of formula (N-1) is:

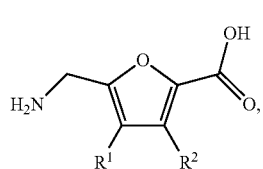

(N-1)

wherein $R^1$ and $R^2$ are as defined for formula (V) above, and the polymer of formula (T) is:

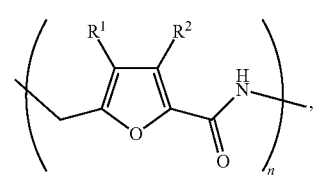

(T)

wherein $R^1$, $R^2$ and n are as defined for formula (V) above;

reducing the polymer of formula (T) to a polymer of formula (U), wherein:

the polymer of formula (U) is:

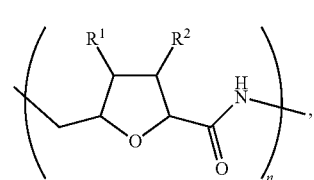

(U)

wherein $R^1$, $R^2$ and n are as defined for formula (V) above; and converting the polymer of formula (U) to the polymer of formula (V).

68. A method of producing a polymer of formula (V):

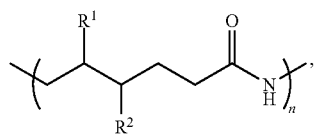
(V)

wherein:
R¹ and R² are each independently hydrogen or alkyl, and n is greater than 1,
the method comprising:
providing a compound of formula (D) produced according to the method of any one of embodiments 1 to 4; and
converting the compound of formula (D) to the polymer of formula (V).

69. A method of producing a polymer of formula (V):

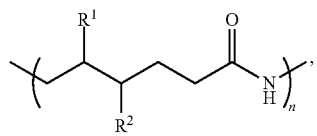
(V)

wherein:
R¹ and R² are each independently hydrogen or alkyl, and n is greater than 1,
the method comprising:
providing a compound of formula (F) produced according to the method of embodiment 8 or 9; and
converting the compound of formula (F) to the polymer of formula (V).

70. A method of producing a polymer of formula (V):

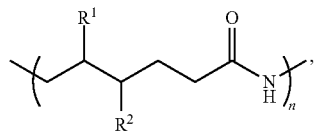
(V)

wherein:
R¹ and R² are each independently hydrogen or alkyl, and n is greater than 1,
the method comprising:
providing a compound of formula (I) produced according to the method of any one of embodiments 11 to 17 and 45 to 54; and
converting the compound of formula (I) to the polymer of formula (V).

71. A method of producing a polymer of formula (V):

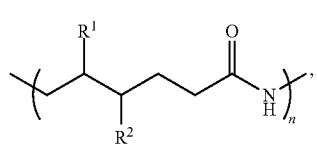
(V)

wherein:
R¹ and R² are each independently hydrogen or alkyl, and n is greater than 1,
the method comprising:
providing a compound of formula (R) produced according to the method of any one of embodiments 55 to 61 and 63 to 66; and
converting the compound of formula (R) to the polymer of formula (V).

72. A method for producing nylon, comprising:
providing:
(i) cyclohexanone according to the method of any one of embodiments 5 to 7, or
(ii) hexane-1,6-diol according to the method of embodiment 10, or
(iii) hexamethylenediamine according to the method of any one of embodiments 18 to 24; or
(iv) caprolactam according to the method of embodiment 62,
or any combination thereof; and
converting the cyclohexanone, the hexane-1,6-diol, the hexamethylenediamine, the caprolactam, or any combination thereof, to nylon.

73. A method for producing nylon having the structure of formula (X):

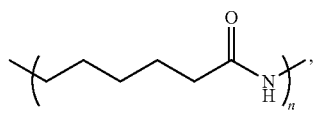
(X)

wherein n is an integer greater than 0;
the method comprising:
converting 5-(halomethyl)furfural to 5-(aminomethyl)furan-2-carboxylic acid; and
polymerizing the 5-(aminomethyl)furan-2-carboxylic acid to form a polymer of formula (X1):

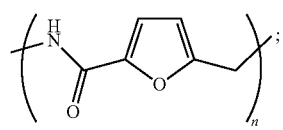
(X1)

reducing the polymer of formula (X1) to form a polymer of formula (X2):

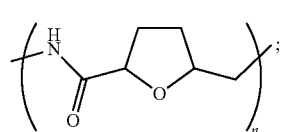
(X2)

and
converting the polymer of formula (X2) to the nylon of formula (X).

74. A polymer of formula (U):

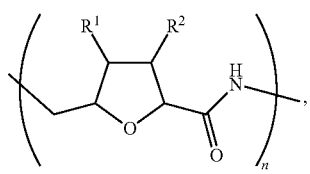

wherein:
R[1] and R[2] are each independently hydrogen or alkyl, and n is greater than 1.

EXAMPLES

The following Examples are merely illustrative and are not meant to limit any aspects of the present disclosure in any way. It should also be understood that the compounds provided in square brackets in the reaction schemes below are intermediates that may, without wishing to be bound by any theory, be formed.

Example 1

Synthesis of Cyclohexanone

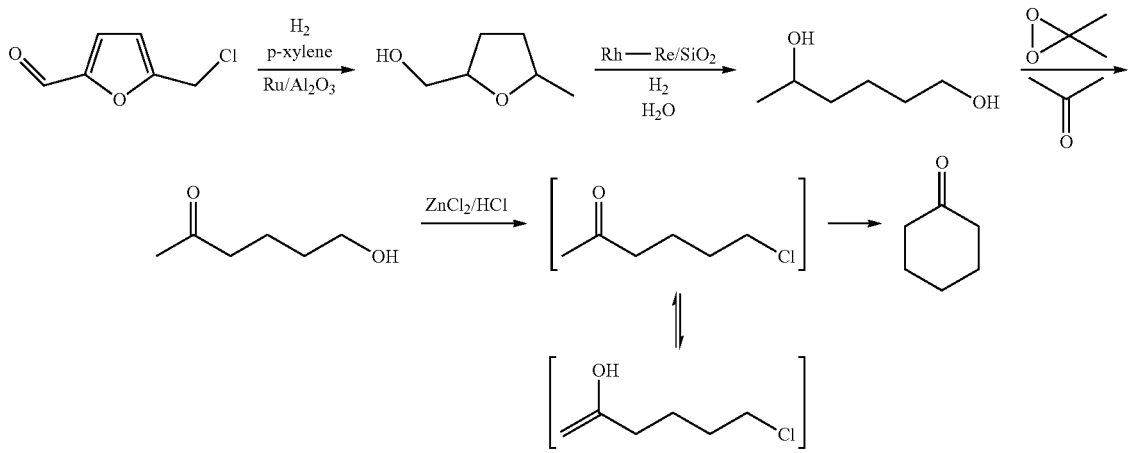

Materials and Methods

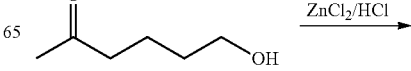

To a parr reactor is added 5-(chloromethyl)furfural and p-xylene followed by Ru/Al$_2$O$_3$. The reactor is then flushed three times with nitrogen and subsequently with hydrogen. After flushing, the reactor is pressurized to 90 bar, and the reaction mixture is stirred and heated to 100° C. for 10 h. Product conversion and selectivity are analyzed by gas phase chromatography (GC). The product is then purified by distillation.

To a parr reactor is added 5-methyltetrahydrofuranalcohol and water followed by Rh—Re/SiO$_2$. The reactor is then flushed three times with nitrogen and subsequently with hydrogen. After flushing, the reactor is pressurized to 80 bar, and the reaction mixture is stirred and heated to 180° C. for 5 h. Product conversion and selectivity are analyzed by GC. The product is then purified by distillation.

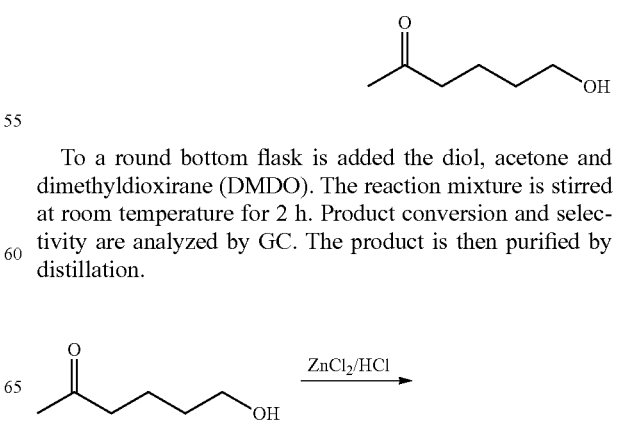

To a round bottom flask is added the diol, acetone and dimethyldioxirane (DMDO). The reaction mixture is stirred at room temperature for 2 h. Product conversion and selectivity are analyzed by GC. The product is then purified by distillation.

-continued

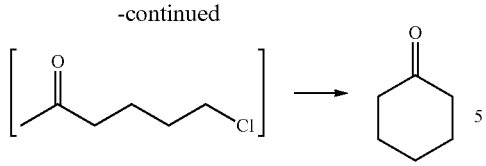

To a round bottom flask is added the keto alcohol compound, toluene and $ZnCl_2$. HCl gas is then introduced into the reaction mixture. The reaction mixture is then stirred at room temperature for 1 h followed by heating to reflux. Product conversion and selectivity are analyzed by GC. The product is then purified by distillation.

Example 2

Synthesis of Cyclohexanone

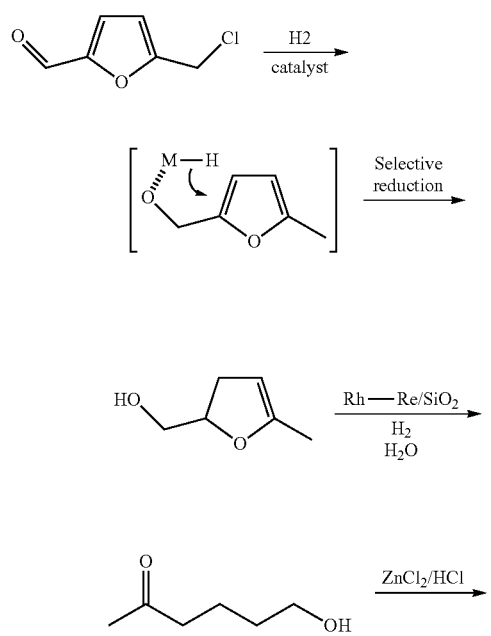

-continued

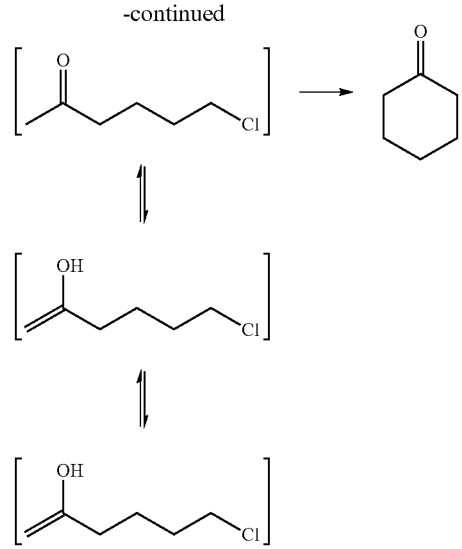

To a parr reactor is added 5-chloromethylfurfural and toluene followed by a catalyst, Pt/C. The reactor is then flushed three times with nitrogen and subsequently with hydrogen. After flushing, the reactor is pressurized to 10 bar, and the reaction mixture is stirred and heated to 100° C. for 5 h. Product conversion and selectivity are analyzed by GC. The product is then purified by distillation or directly transferred into another parr reactor containing the catalyst Rh—Re/$SiO_2$ and water. This reactor is pressurized to 80 bar, and the reaction mixture is stirred and heated to 120° C. for 5 h which gives the keto-alcohol product.

The subsequent conversion of 6-hydroxyhexan-2-one to cyclohexanone, as illustrated in the reaction scheme above, is performed according to the procedure set forth in Example 1 above.

Example 3

Synthesis of 1,6-Hexanediamine

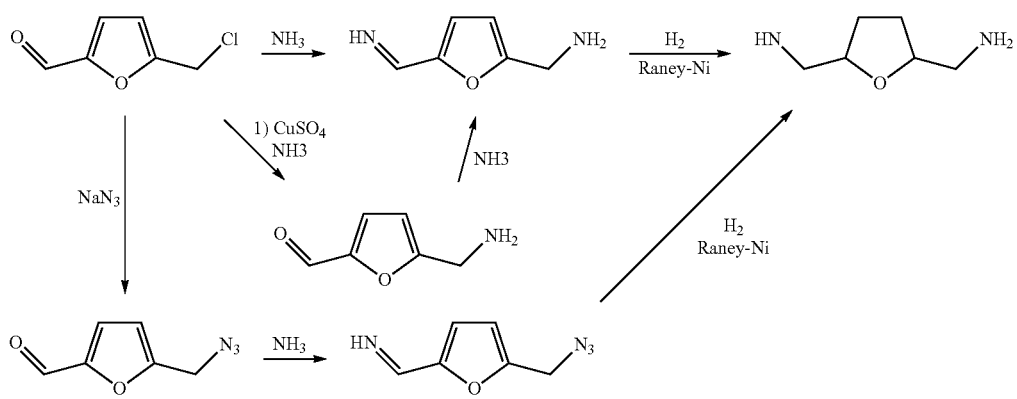

Materials and Methods

The following reactions are alternative methods of producing (5-(iminomethyl)furan-2-yl)methanamine.

Alternative #1:

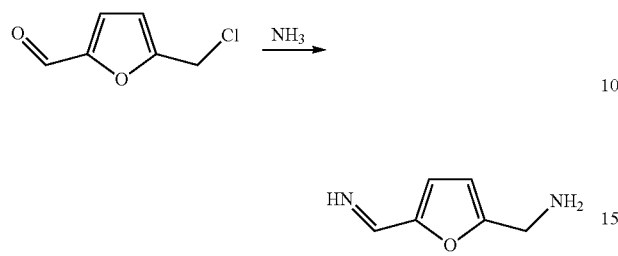

A round bottom flask equipped with a stir bar is cooled to −56° C. with a dry ice/n-octane bath and equipped with a cold finger condenser cooled with a dry ice/n-octane mixture. Ammonia gas is slowly introduced into the setup which will be trapped in its liquid form. Then 5-chloromethylfurfural is slowly added dropwise to liquid ammonia which behaves as a solvent and a reagent. After stiffing for 1-2 hours, the ammonia is evacuated from the flask while warming up the flask to room temperature. The resulting residue is directly used in the following reduction reaction.

Alternative #2:

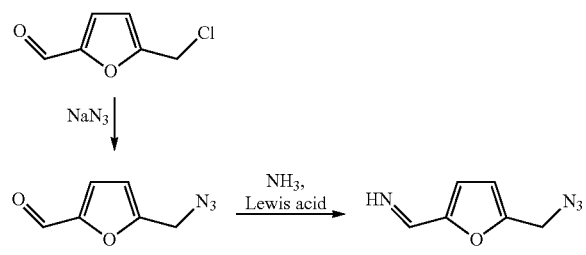 [SMILES: O=Cc1ccc(CCl)o1 ; [N-]=[N+]=NCc1ccc(C=O)o1 ; "NH3,Lewis acid" ; [N-]=[N+]=NCc1ccc(C=N)o1 ; "NaN3"]

To a round bottom flask equipped with a stir bar is added 5-(chloromethyl)furfural (CMF) and toluene. The reaction mixture is cooled to 0° C. and NaN$_3$ is slowly added. The reaction mixture is slowly warmed up to room temperature until complete CMF conversion is achieved. The resulting NaCl salt is then filtered off from the reaction mixture. Then toluene is evaporated to yield the azide aldehyde product.

Then, to a round bottom flask equipped with a stir bar is added the azide aldehyde residue and EtOH. This flask is then cooled to −56° C. with a dry ice/n-octane bath and equipped with a cold finger condenser cooled with a dry ice/n-octane mixture. Ammonia gas is slowly introduced into the setup which will be trapped in its liquid form. After stiffing for 1-2 hours, the ammonia is evacuated from the flask while warming up the flask to room temperature. The resulting residue is directly used in the subsequent reduction reaction.

Alternative #3:

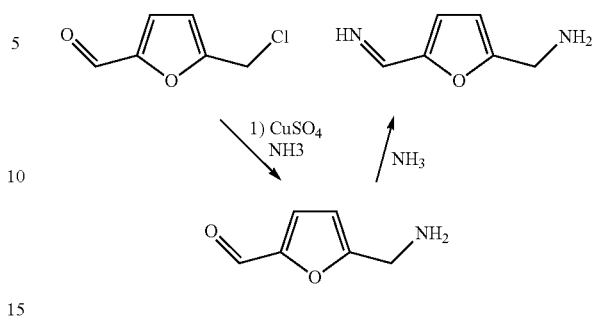

To a parr reactor is added 5-chloromethylfurfural (CMF), CuSO$_4$, PEG$_{1000}$-DIL and dioxane. The reactor is then flushed three times with nitrogen and subsequently with NH$_3$. After flushing, the reactor is pressurized to 1 bar, and the reaction mixture is stirred and heated to 60° C. for 3 h. After cooling down the parr reactor, the reaction mixture is concentrated.

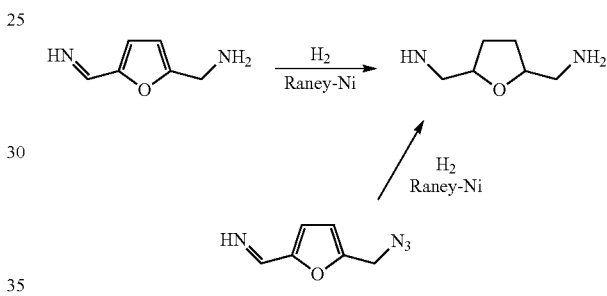

To a parr reactor is added the imine compound, dried p-xylene and Raney-Ni. The reactor is then flushed three times with nitrogen and subsequently with hydrogen. After flushing, the reactor is pressurized to 90 bar, and the reaction mixture is stirred and heated to 100° C. for 10 h. Product conversion and selectivity are analyzed by a reverse phase high-performance liquid chromatography (HPLC). The crude reaction mixture is carried over to the next reaction.

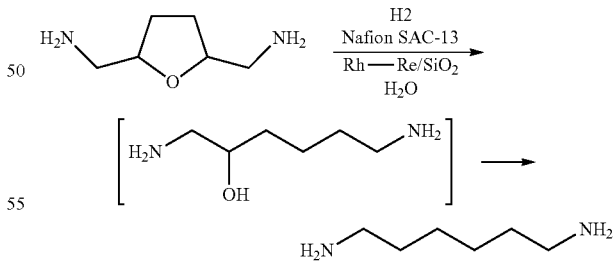

The diamine crude compound, Rh—Re/SiO$_2$ catalyst, water, Nafion SAC-13 are added to a parr reactor. The reactor is then flushed three times with nitrogen and subsequently with hydrogen. After flushing, the reactor is pressurized to 10 bar, and the reaction mixture is stirred and heated to 80° C. for 10 h. Product conversion and selectivity are analyzed by gas chromatography-mass spectrometry (GCMS).

Example 4

Synthesis of 1,6-Hexanediol

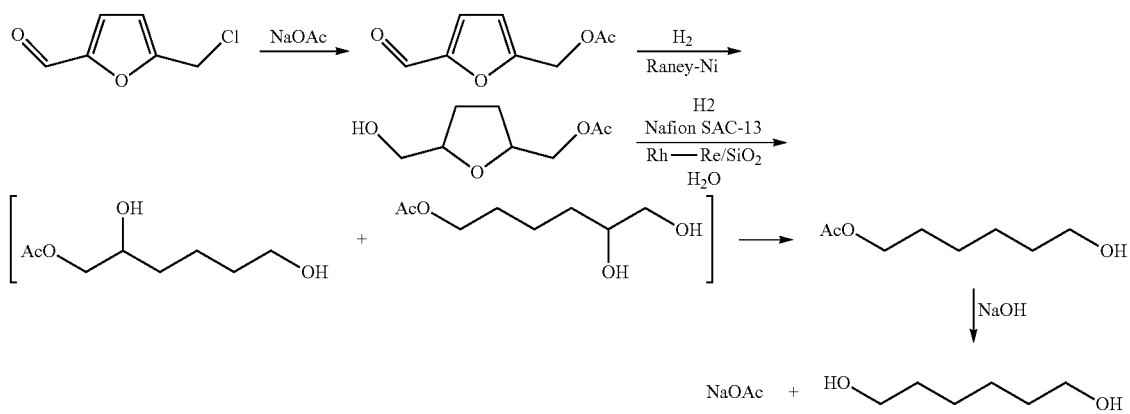

Materials and Methods

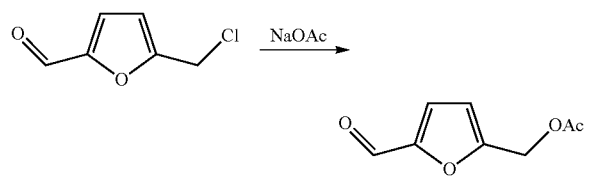

To a round bottom flask equipped with a stir bar and a condenser is added 5-chloromethylfurfural (CMF), sodium acetate (NaOAc) and p-xylene. The reaction mixture is heated to reflux until all NaCl is observed to crash out of the solution. The crude solution is then filtered and directly transferred in the parr reactor for next step.

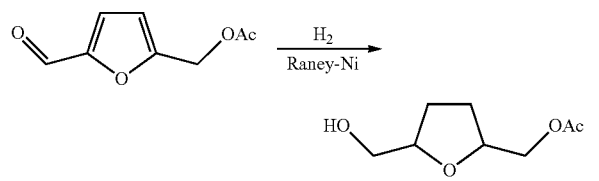

A parr reactor is loaded with the previous crude solution and Raney-Ni. The reactor is then flushed three times with nitrogen and subsequently with hydrogen. After flushing, the reactor is pressurized to 90 bar, and the reaction mixture is stirred and heated to 100° C. for 10 h. Product conversion and selectivity are analyzed by reverse phase HPLC. The crude reaction mixture is concentrated under vacuum.

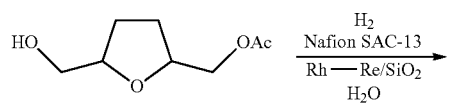

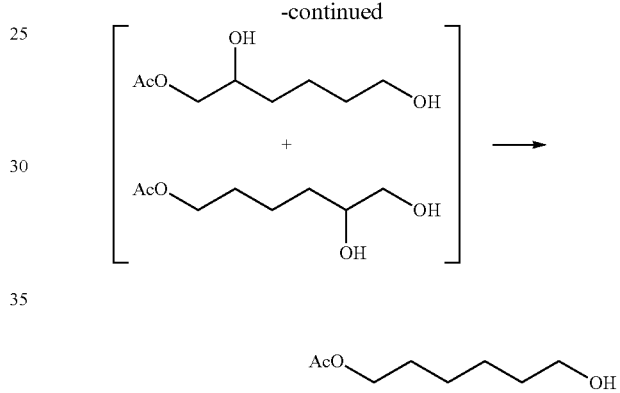

The previous crude residue, Rh—Re/SiO$_2$ catalyst, Nafion SAC-13 and water are added to a parr reactor. The reactor is then flushed three times with nitrogen and subsequently with hydrogen. After flushing, the reactor is pressurized to 10 bar, and the reaction mixture is stirred and heated to 80° C. for 10 h. Product conversion and selectivity are analyzed by GCMS. The crude reaction mixture is carried over to the next reaction.

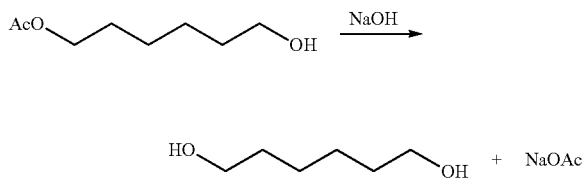

To a round bottom flask equipped with a stir bar and a condenser is added the crude reaction mixture (acetate compound in p-xylene) and NaOH. The mixture is heated to reflux until all NaOAc crashed out. Product conversion and selectivity are analyzed by GCMS. The diol is purified from the reaction solvent by phase separation.

Example 5

Synthesis of Caprolactam

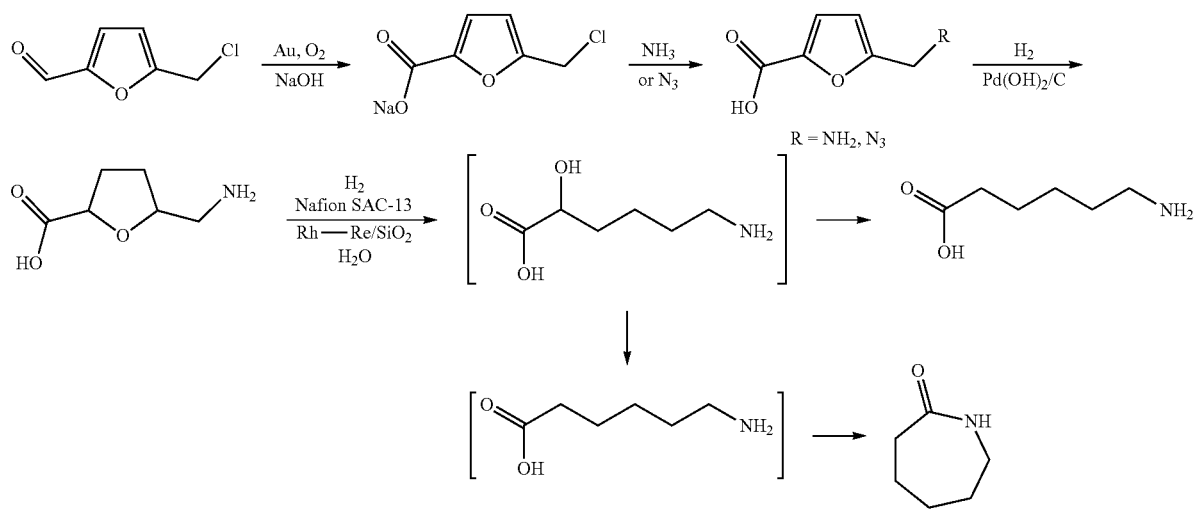

Materials and Methods

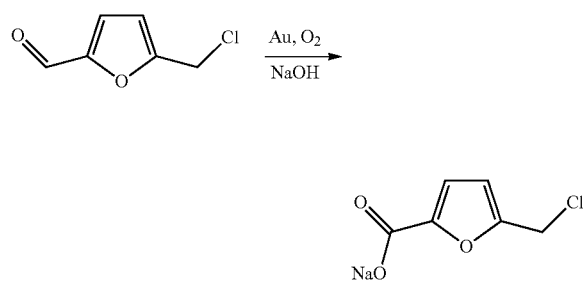

To a parr reactor is added 5-chloromethylfurfural (CMF), Au, sodium hydroxide (NaOH) and tetrahydrofuran (THF). The reactor is then flushed three times with nitrogen and subsequently with oxygen. After flushing, the reactor is pressurized to 3 bar, and the reaction mixture is stirred and heated to 60° C. for 4 h. The furancarboxylate salt is separated from the solvent by filtration.

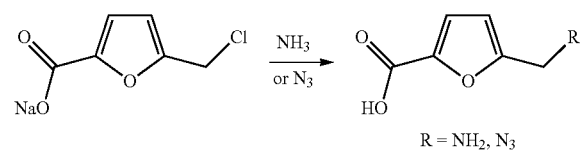

With $NH_3$: A round bottom flask equipped with a stir bar is cooled to −56° C. with a dry ice/n-octane bath and equipped with a cold finger condenser cooled with a dry ice/n-octane mixture. Ammonia gas is slowly introduced into the setup which will be trapped in its liquid form. Then 5-(chloromethyl)furancarboxylate is slowly added to liquid ammonia. After stiffing for 1-2 hours, the ammonia is evacuated from the flask while warming up the flask to room temperature. The resulting residue is directly used in the following reduction reaction or purified by recrystallization.

With $N_3$: To a round bottom flask equipped with a stir bar is added 5-(chloromethyl)furancarboxylate and DMF. The reaction mixture is cooled to 0° C. and $NaN_3$ is slowly added. The reaction mixture is slowly warmed up to room temperature and then heated to 80° C. for 4 h. The resulting NaCl salt is then filtered off from the reaction mixture. The resulting residue is directly used in the following reduction reaction.

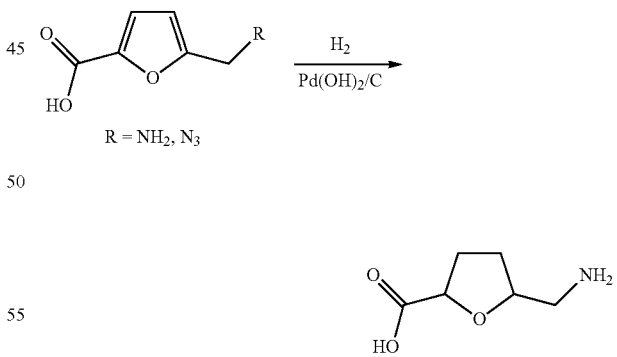

A parr reactor is loaded with the previous crude solution and $Pd(OH)_2/C$. The reactor is then flushed three times with nitrogen and subsequently with hydrogen. After flushing, the reactor is pressurized to 3 bar, and the reaction mixture is stirred and heated to 50° C. for 1 h. Product conversion and selectivity are analyzed by reverse phase HPLC. The crude reaction mixture is used as it is in the next step or the product can also be purified by recrystallization.

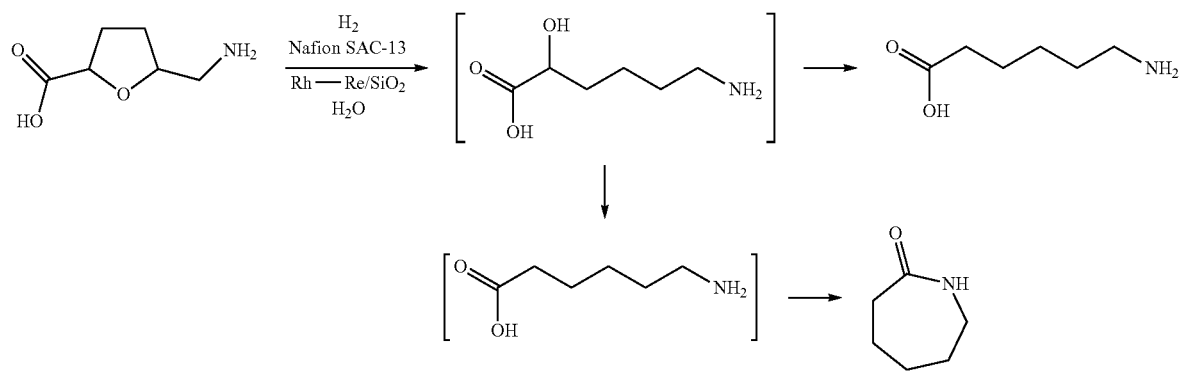

The previous reaction mixture (or purified product), Rh—Re/SiO$_2$ catalyst, Nafion SAC-13 are added to a parr reactor. The reactor is then flushed three times with nitrogen and subsequently with hydrogen. After flushing, the reactor is pressurized to 10 bar, and the reaction mixture is stirred and heated to 80° C. for 10 h. Product conversion and selectivity are analyzed by GCMS. Either open or closed form of caprolactam can be obtained in this reaction.

Example 6

Synthesis of Nylon-6

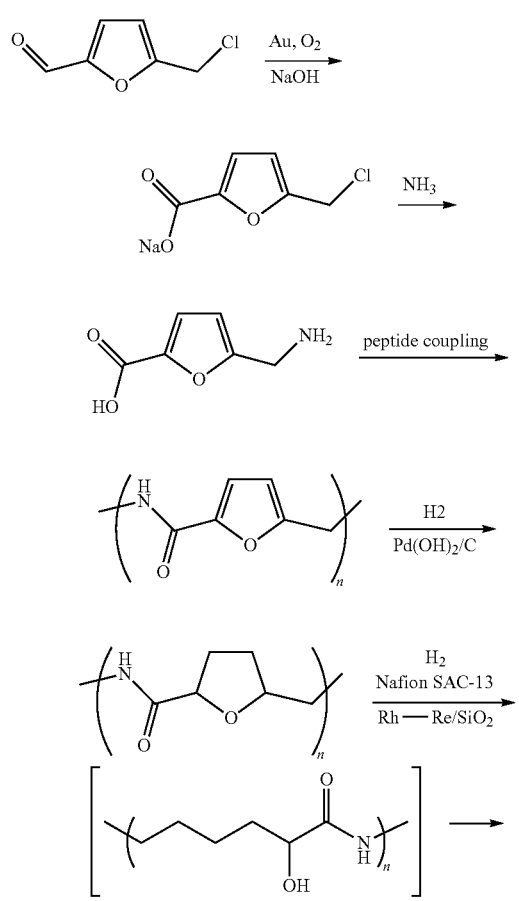

-continued

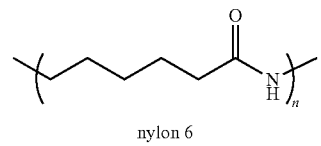

nylon 6

Materials and Methods

To a parr reactor is added 5-chloromethylfurfural (CMF), Au, NaOH and THF. The reactor is then flushed three times with nitrogen and subsequently with oxygen. After flushing, the reactor is pressurized to 3 bar, and the reaction mixture is stirred and heated to 60° C. for 4 h. The furancarboxylate salt is purified by simple filtration out of the solvent.

A round bottom flask equipped with a stir bar is cooled to −56° C. with a dry ice/n-octane bath and equipped with a cold finger condenser cooled with a dry ice/n-octane mixture. Ammonia gas is slowly introduced into the setup which will be trapped in its liquid form. Then 5-(chloromethyl)furancarboxylate is slowly added to liquid ammonia. After stiffing for 1-2 hours, the ammonia is evacuated from the flask while warming up the flask to room temperature. Solvent is evaporated and the resulting residue is purified by recrystallization.

59

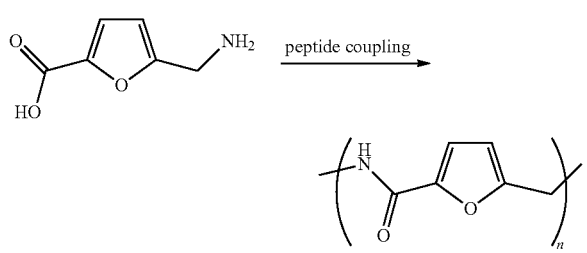

To a round bottom flask equipped with a stir bar and a dean-stark trap is added the furan-amino acid and toluene. The reaction mixture is stirred and heated to reflux until most of the water has been removed. The crude reaction is then concentrated and washed continuously with water to remove any amino acids residue to yield a purified furan amide polymer.

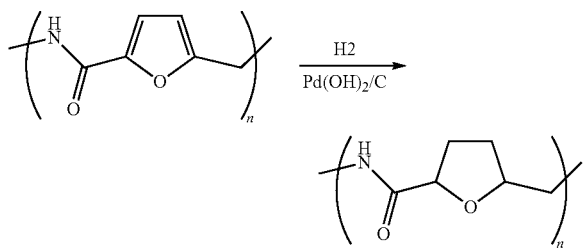

A parr reactor is loaded with the previous crude solution and $Pd(OH)_2/C$. The reactor is then flushed three times with nitrogen and subsequently with hydrogen. After flushing, the reactor is pressurized to 3 bar, and the reaction mixture is stirred and heated to 50° C. for 1 h. Product conversion and selectivity are analyzed by reverse phase HPLC. The crude reaction mixture is used as it is in the next step or the product can also be purified by recrystallization.

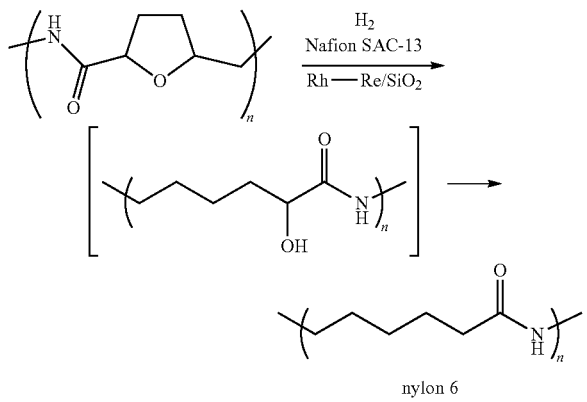

nylon 6

The previous reaction mixture (tetrahydrofuran amide polymer in DMF), Rh—Re/SiO$_2$ catalyst, Nafion SAC-13 are added to a parr reactor. The reactor is then flushed three times with nitrogen and subsequently with hydrogen. After flushing, the reactor is pressurized to 10 bar, and the reaction mixture is stirred and heated to 80° C. for 10 h. Nylon 6 is then purified by continuous washing with DMF.

60

Example 7A

Synthesis of 5-(Aminomethyl)furan-2-carbaldehyde

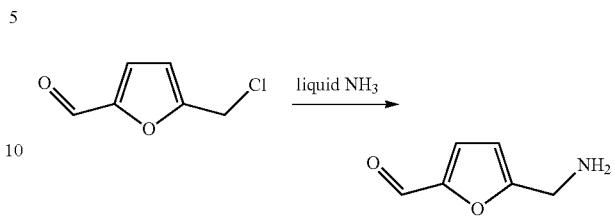

This example demonstrates the synthesis of 5-(aminomethyl)furan-2-carbaldehyde from 5-(chloromethyl)furfural (CMF).

Apparatus setup: Ammonia gas was delivered to an empty 3-neck flask through a sparge stone, which was connected to another 3-neck round bottom flask (reaction flask) equipped with a dewar condenser and a stir bar. The dewar condenser was connected from the top to another 2-neck empty flask, which was connected to a water bubbler for ammonia trapping.

The apparatus was first flame dried and flushed under inert gas before introduction of ammonia gas. The reaction flask was cooled to −40° C. using an acetonitrile/dry ice bath and the dewar condenser was cooled to −78° C. using acetone/dry ice. The ammonia was then introduced into the system at 1-2 psi until 70 ml of liquid ammonia was condensed into the reaction flask. Then, solid CMF (0.202 g) was introduced. The reaction mixture was stirred for 1.5 h. An aliquot of the reaction mixture was diluted in acetonitrile and was analyzed by electrospray ionization mass spectrometry (ESI-MS).

The formation of 5-(aminomethyl)furan-2-carbaldehyde was confirmed by the ESI-MS data. ESI-MS calculated for $C_6H_7NO_2$ [M]: 125.1; Observed: [M+H]: 126.2.

Example 7B

Synthesis of 5-(Aminomethyl)furan-2-carbaldehyde

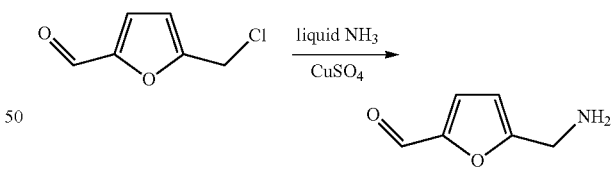

This example also demonstrates the synthesis of 5-(aminomethyl)furan-2-carbaldehyde from 5-(chloromethyl)furfural (CMF).

The same apparatus setup as Example 7A above was used in this example. The apparatus was first flame dried and flushed under inert gas before introduction of ammonia gas. The reaction flask was cooled to −40° C. using an acetonitrile/dry ice bath and the dewar condenser was cooled to −78° C. using acetone/dry ice. The ammonia was then introduced into the system at 1-2 psi until 70 ml of liquid ammonia was condensed into the reaction flask. Then, solid CMF (0.202 g) was introduced. The reaction mixture was allowed to stir for 2 h, and then CuSO$_4$ (6.6 mg, 3%) was added. The reaction mixture was allowed to stir for an additional 40 minutes. An aliquot of the reaction mixture was diluted in acetonitrile and was analyzed by ESI-MS.

The formation of 5-(aminomethyl)furan-2-carbaldehyde was confirmed by the ESI-MS data. Observed: [M+H]: 126.2.

Example 7C

Synthesis of 5-(Aminomethyl)furan-2-carbaldehyde

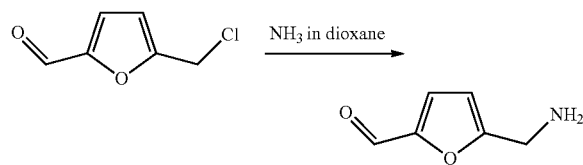

This example also demonstrates the synthesis of 5-(aminomethyl)furan-2-carbaldehyde from 5-(chloromethyl)furfural (CMF).

To a screw cap vial was added 186.9 mg of CMF, followed by 5.4 ml of 0.5 M $NH_3$ in dioxane. The reaction mixture was stirred for 2 h at 20° C. An aliquot of the reaction mixture was diluted in acetonitrile and was analyzed by ESI-MS.

The formation of 5-(aminomethyl)furan-2-carbaldehyde was confirmed by the ESI-MS data. Observed [M+H]: 126.2.

Example 7D

Synthesis of 5-(Aminomethyl)furan-2-carbaldehyde

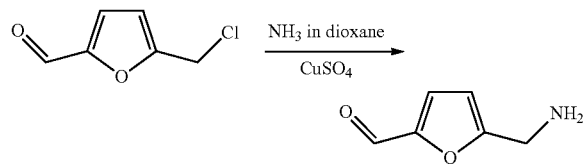

This example also demonstrates the synthesis of 5-(aminomethyl)furan-2-carbaldehyde from 5-(chloromethyl)furfural (CMF).

To a screw cap vial was added 186.9 mg of CMF, followed by 5.4 ml of 0.5 M $NH_3$ in dioxane. The reaction mixture was stirred for 2 h at 20° C. Then, 21 mg of $CuSO_4$ was added to the reaction mixture, and the reaction mixture was stirred for an additional 1 h. An aliquot of the reaction mixture was diluted in acetonitrile and was analyzed by ESI-MS.

The formation of 5-(aminomethyl)furan-2-carbaldehyde was confirmed by the ESI-MS data. Observed [M+H]: 126.2.

Example 8

Synthesis of Chloride Salt of 5-(Aminomethyl)furan-2-carbaldehyde

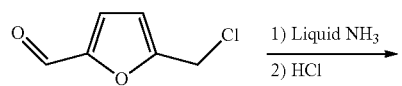

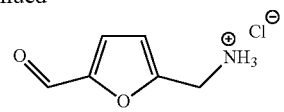

This example demonstrates the synthesis of a chloride salt of 5-(aminomethyl)furan-2-carbaldehyde from 5-(chloromethyl)furfural (CMF). The chloride salt is also referred to as (5-formylfuran-2-yl)methanaminium chloride.

The same apparatus setup as Example 7A above was used in this example. The apparatus was first flame dried and flushed under inert gas before introduction of ammonia gas. The reaction flask was cooled to −40° C. using an acetonitrile/dry ice bath and the dewar condenser was cooled to −78° C. using acetone/dry ice. The ammonia was then introduced into the system at 1-2 psi until 30-40 ml of liquid ammonia was condensed into the reaction flask. Then, solid CMF (1.16 g) was introduced. The reaction mixture was allowed to stir for 5 minutes at −40° C. Then, the bath was removed and the reaction flask was allowed to warm up to room temperature under air (20° C.), while the ammonia was observed to slowly evaporate over 26 min. At that time, an orange/red solid was visible at the bottom of the flask. THF was added (18 ml) and the mixture was filtered through a Büchner funnel. The solid residue was sequentially washed with dichloromethane (DCM; 50 ml), water (50 ml) and acetone (50 ml) and was allowed to dry under air.

The residue was then dissolved with 6 M HCl and purified on cellulose column chromatography using eluent methanol (MeOH)/acetic acid (AcOH)/water (4:2:1). The product fractions were eluted on paper chromatography and checked by ninhydrin stain (reddish orange spot, $R_f$=0.9, MeOH/AcOH/water (4:2:1)). The combined fractions were then concentrated to yield a solid (569 mg, 44% yield). The structure of the solid was analyzed by $^1H$ NMR and ESI-MS.

The formation of the chloride salt of 5-(aminomethyl)furan-2-carbaldehyde was confirmed by the $^1H$ NMR and ESI-MS data.

$^1H$ NMR (600 MHz, deuterium oxide) δ ppm: 4.25 (s, 2H) 6.72 (d, J=3.52 Hz, 1H) 6.95 (br s, 1H) 7.02-7.05 (m, 1H) 7.12 (br s, 1H) 7.43 (d, J=4.11 Hz, 1H) 9.39 (s, 1H).

ESI-MS calculated for $C_6H_7NO_2$ [M]: 125.1; Observed [M+H]: 126.2.

What is claimed is:

1. A method of producing a compound of formula (J):

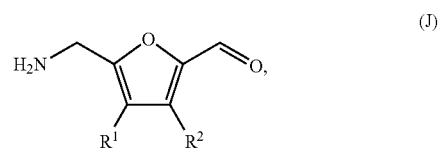

and/or a salt thereof, wherein $R^1$ and $R^2$ are each independently hydrogen or alkyl, the method comprising:

combining a compound of formula (A) with ammonia in the presence of a copper catalyst to produce the compound of formula (J) and/or a salt thereof, wherein:

the compound of formula (A) is:

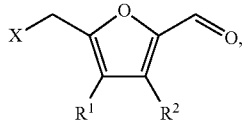

(A)

wherein:
R$^1$ and R$^2$ are as defined for formula (J) above, and
X is halo.

2. The method of claim 1, wherein the salt of the compound of formula (J) is a compound of formula (J-X):

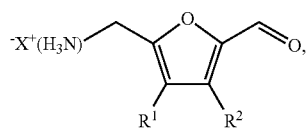

(J-X)

wherein:
R$^1$ and R$^2$ are as defined for formula (J) above, and
X is as defined for formula (A) above.

3. A method of producing a compound of formula (J-X):

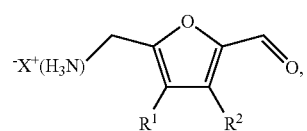

(J-X)

wherein:
R$^1$ and R$^2$ are each independently hydrogen or alkyl, and
X is halo,
the method comprising:
combining a compound of formula (A) with liquid ammonia and acid to produce the compound of formula (J-X), wherein:
the acid is a Bronsted acid with a pKa equal to or lower than 9; and
the compound of formula (A) is:

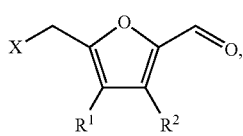

(A)

wherein:
R$^1$ and R$^2$ are as defined for formula (J-X) above, and
X is halo.

4. The method of claim 3, wherein the acid is HY, wherein Y is halo, and the method further comprises:
producing a compound of formula (J-Y) from at least a portion of the reaction mixture, wherein the compound of formula (J-Y) is:

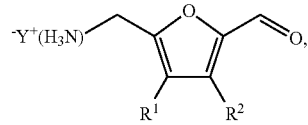

(J-Y)

wherein:
R$^1$ and R$^2$ are as defined for formula (J-X) above, and
Y is as defined for the acid.

5. A method of producing a compound of formula (J-X):

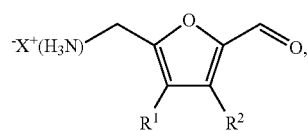

(J-X)

wherein:
R$^1$ and R$^2$ are each independently hydrogen or alkyl, and
X is halo,
the method comprising:
combining a compound of formula (A) with ammonia and a copper catalyst to produce a compound of formula (J) in a reaction mixture, wherein:
the compound of formula (A) is:

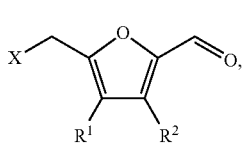

(A)

wherein:
R$^1$ and R$^2$ are as defined for formula (J-X) above, and
X is halo; and
the compound of formula (J) is:

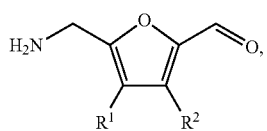

(J)

wherein R$^1$ and R$^2$ are as defined for formula (J-X) above; and
adding an acid to the reaction mixture of step (b) to produce the compound of formula (J-X), wherein the acid is a Bronsted acid with a pKa equal to or lower than 9.

6. The method of claim 5, wherein the acid is HY, wherein Y is halo, and wherein the adding of the acid to the reaction mixture of step (b) produces the compound of formula (J-X), or a compound of formula (J-Y), or a combination thereof, wherein the compound of formula (J-Y) is:

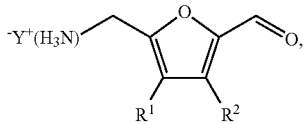

wherein:
R$^1$ and R$^2$ are as defined for formula (J-X) above, and
Y is as defined for the acid.

7. A method of producing a compound of formula (J-X):

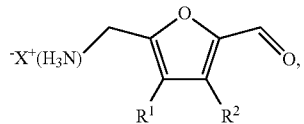

wherein:
R$^1$ and R$^2$ are each independently hydrogen or alkyl, and
X is halo,
the method comprising:
  a) combining a compound of formula (A) with ammonia and a copper catalyst to form a reaction mixture, wherein:
  the compound of formula (A) is:

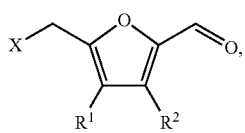

wherein:
  R$^1$ and R$^2$ are as defined for formula (J-X) above, and
  X is halo;
  b) producing a compound of formula (J) from at least a portion of the reaction mixture, wherein the compound of formula (J) is:

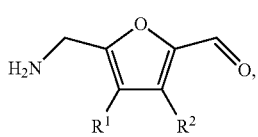

wherein R$^1$ and R$^2$ are as defined for formula (J-X) above; and
  c) isolating the compound of formula (J) produced; and
  d) combining the isolated compound of formula (J) with an acid to produce the compound of formula (J-X), wherein the acid is a Bronsted acid with a pKa equal to or lower than 9.

8. The method of claim 7, wherein the acid is HY, wherein Y is halo, and wherein the combining of the isolated compound of formula (J) with the acid produces the compound of formula (J-X), or a compound of formula (J-Y), or a combination thereof, wherein the compound of formula (J-Y) is:

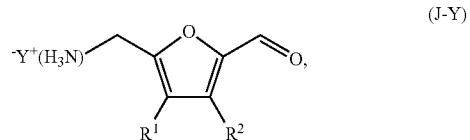

wherein:
R$^1$ and R$^2$ are as defined for formula (J-X) above, and
Y is as defined for the acid.

9. A method of producing a compound of formula (I):

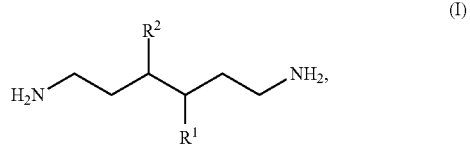

and/or a salt thereof, wherein R$^1$ and R$^2$ are each independently hydrogen or alkyl,
the method comprising:
  producing a compound of formula (J) and/or a salt thereof according to the method of claim 1, wherein:
  the compound of formula (J) is:

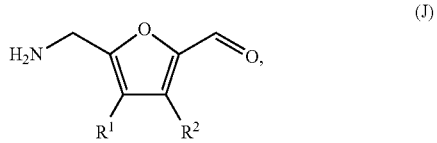

and/or a salt thereof, wherein R$^1$ and R$^2$ are as defined for formula (I) above; and
  reducing the compound of formula (J) and/or a salt thereof in the presence of additional ammonia to produce the compound of formula (H) and/or a salt thereof, wherein:
  the compound of formula (H) is:

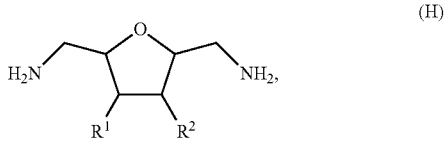

wherein R$^1$ and R$^2$ are as defined for formula (I) above; and
  further reducing the compound of formula (H) and/or a salt thereof to produce the compound of formula (I) and/or a salt thereof.

* * * * *